United States Patent
Hirose et al.

(10) Patent No.: US 9,752,135 B2
(45) Date of Patent: Sep. 5, 2017

(54) THERMOSTABLE β-GLUCOSIDASE

(71) Applicant: HONDA MOTOR CO., LTD., Minato-ku, Tokyo (JP)

(72) Inventors: Yoshitsugu Hirose, Wako (JP); Takahiro Gunji, Wako (JP); Asuka Yamaguchi, Wako (JP); Migiwa Suda, Wako (JP); Jiro Okuma, Wako (JP); Yasuhiro Kondo, Wako (JP); Tomohiko Kato, Kisarazu (JP); Daisuke Shibata, Kisarazu (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 14/850,732

(22) Filed: Sep. 10, 2015

(65) Prior Publication Data
US 2016/0076016 A1 Mar. 17, 2016

(30) Foreign Application Priority Data
Sep. 11, 2014 (JP) ................. 2014-184909

(51) Int. Cl.
| | |
|---|---|
| C12N 9/24 | (2006.01) |
| C12P 19/14 | (2006.01) |
| C12N 1/20 | (2006.01) |
| C12N 5/00 | (2006.01) |
| C12N 5/02 | (2006.01) |
| C07H 21/04 | (2006.01) |
| C12N 9/42 | (2006.01) |
| C12P 19/02 | (2006.01) |

(52) U.S. Cl.
CPC ......... *C12N 9/2445* (2013.01); *C12N 9/2482* (2013.01); *C12P 19/02* (2013.01); *C12P 19/14* (2013.01); *C12Y 302/01008* (2013.01); *C12Y 302/01021* (2013.01); *C12P 2203/00* (2013.01)

(58) Field of Classification Search
None
See application file for complete search history.

(56) References Cited

U.S. PATENT DOCUMENTS

| | | | | |
|---|---|---|---|---|
| 9,512,414 | B2 * | 12/2016 | Okuma | C12P 19/02 |
| 2004/0091469 | A1 * | 5/2004 | Fukasawa | C12N 9/2445 |
| | | | | 424/94.61 |

FOREIGN PATENT DOCUMENTS

| | | |
|---|---|---|
| JP | 10-052274 A | 2/1998 |
| JP | 4689807 B2 | 5/2011 |
| JP | 4801872 B2 | 10/2011 |
| WO | 9725417 A1 | 7/1997 |

OTHER PUBLICATIONS

Office Action Search Report mailed Nov. 27, 2015 corresponding to Patent Application No. EP15184676.3.

Yernool et al., "Cloning and Characterization of the Glucooligosaccharide Catabolic Pathway Beta-Glucan Glucohydrolase and Cellobiose Phosphorylase in the Marine Hyperthermophile Thermotoga neapolitana," Journal of Bacteriology, Sep. 2000, pp. 5172-5179, vol. 182, No. 18, American Society for Microbiology.

Gao, et al., "Purification and Characterization of a New Beta-Glucosidase from Penicillium piceum and its Application in Enzymatic Degradation of Delignified Corn Stover," Bioresource Technology, 2013, pp. 658-661, vol./Issue 147, Elsevier Ltd.

Dotsenko et al., "Characterization of a GH Family 3 Beta-Glycoside Hydrolase from Chrysosporium lucknowense and its Application to the Hydrolysis of Beta-Glucan and Xylan," Bioresource Technology, 2012, pp. 345-349, vol./Issue 112, Elsevier Ltd.

Schroder et al., "Characterization of a Heat-Active Archaeal Beta-Glucosidase From a Hydrothermal Spring Metagenome," Enzyme and Microbial Technology, 2014, pp. 48-54, vol./Issue 57, Elsevier Ltd.

Zhou et al., "Beta-Xylosidase Activity of a GH3 Glucosidase/Xylosidase From Yak Rumen Metagenome Promotes the Enzymatic Degradation of Hemicellulosic Xylans," Letters in Applied Microbiology, 2011, pp. 79-87, vol./Issue 54, The Society for Applied Microbiology.

Parry et al., "Biochemical characterization and mechanism of action of a thermostable Beta-glucosidase purified from Thermoascus aurantiacus", Biochemical Journal, 2001, vol. 353, p. 117-127.

Jabbour et al., "A novel thermostable and glucose-tolerant Beta-glucosidase from Fervidobacterium islandicum", Applied Microbiology and Biotechnology, 2012, vol. 93, p. 1947-1956.

Quinlan et al., "Pyrobayes: an improved base caller for SNP discovery in pyrosequences", Nature Methods, 2008, vol. 5, p. 179-181.

Noguchi et al., "MegaGeneAnnotator: Detecting Species-Specific Patterns of Ribosomal Binding Site for Precise Gene Prediction in Anonymous Prokaryotic and Phage Genomes", DNA Research 15,, 2008,15(6), p. 387-396.

Finn et al., "the Pfam protein families database", Nucleic Acids Research Database, 2010, vol. 38, Database issue p. D211-D222.

Durbin et al., 'The theory behind profile HMMs. Biological sequence analysis: probabilistic models of proteins and nucleic acids', 1998, Cambridge University Press.

* cited by examiner

*Primary Examiner* — Iqbal H Chowdhury

(74) *Attorney, Agent, or Firm* — Carrier Blackman & Associates, P.C.; Joseph P. Carrier; Fulchand P. Shende

(57) ABSTRACT

A thermostable β-glucosidase including a β-glucosidase catalytic domain, the β-glucosidase catalytic domain including:
(A) a polypeptide including an amino acid sequence represented by SEQ ID NO: 1;
(B) a polypeptide including an amino acid sequence in which at least one amino acid is deleted, substituted, or added in the amino acid sequence represented by SEQ ID NO: 1, and having hydrolytic activity using p-nitrophenyl-β-D-glucopyranoside as a substrate at least under conditions of a temperature of 75° C. and a pH of 7; or
(C) a polypeptide including an amino acid sequence having at least 90% sequence identity with the amino acid sequence represented by SEQ ID NO: 1, and having hydrolytic activity using p-nitrophenyl-β-D-glucopyranoside as a substrate at least under conditions of a temperature of 75° C. and a pH of 7.

5 Claims, 5 Drawing Sheets

FIG. 1

| | | |
|---|---|---|
| 1. OJIG-364 | 1 MIKRSDFPKNEYFGTATAAYQIEGAANEDGLGPSIWDIFSHTPGKIMITGENGDVA | 55 |
| 2. beta-glucosidase [Fervidobacterium sp. YNP] | 1 MIIRSDFPKDFFFGTATAAYQIEGAANEDGKGPSIWDYFSHTPGKTINGDTGDVA | 55 |
| 1. OJIG-364 | 56 CDHYHRYKEDVQLMKEIGLDAYRFSISWPRMPDGKNINQKGVDFYNRLVDELL | 110 |
| 2. beta-glucosidase [Fervidobacterium sp. YNP] | 56 CDHYHRIKEDIQLMKEIGLDAYRFSISWPRMPDGKNINQKGVDFYNRLVDELLK | 110 |
| 1. OJIG-364 | 111 DIITPEITLYHVDLPYALYEKGGWLNSDLAMYFRAYATFMFNELGDRVKHWITLN | 165 |
| 2. beta-glucosidase [Fervidobacterium sp. YNP] | 111 NDIIPFYITLYHVDLPYALYEKGGWLNPDIALYFRAYATFMFNELGDRVKHWITLN | 165 |
| 1. OJIG-364 | 166 EPWCSSFLGYITGEHAPGHINLQEAIYAAHNLLRSHGHAVQSFREEVKDGTIGLT | 220 |
| 2. beta-glucosidase [Fervidobacterium sp. YNP] | 166 EPWCSSFLGYITGEHAPGHINLQEAIAAHNLLRHGHAVQLFREEVKDGKYGLT | 220 |
| 1. OJIG-364 | 221 NAVVMKTEPGDSRPESELAASLVDKFVNAWFHDPVVFGKYPEEAVKIYQERGLQVM | 275 |
| 2. beta-glucosidase [Fervidobacterium sp. YNP] | 221 NAVVMKIEPGDAKPESELVASLVDKFVNAWFHDPVVFGKVPEEAVAYTEKGLQVP | 275 |
| 1. OJIG-364 | 276 ENDMDIISTPDFEGVNYYIRLVVEDTTNPLGFSYVQGDLPKTEMGWEIYPQGL | 330 |
| 2. beta-glucosidase [Fervidobacterium sp. YNP] | 276 DSSDMKIISTPDFFGVNYYIRLVVEDMNNPLEGFSYVQGDLPKTEMGWEIYPQGL | 330 |
| 1. OJIG-364 | 331 EDMLVTLKERYIEPLYITENGMAGPDKIENGKVKDTYRIEYLEKHFEEKALEAINA | 385 |
| 2. beta-glucosidase [Fervidobacterium sp. YNP] | 331 EDMLVYLKERYILPLYITENGMAGPDKIENGRVHDNYRIEYLEKHFEKALEAINA | 385 |
| 1. OJIG-364 | 386 GVINLKGYFIWSLMDNFEWAYGYSKRFGITVDYNIQKRILKDSAYWLKDFLIS* | 438 |
| 2. beta-glucosidase [Fervidobacterium sp. YNP] | 386 GVIDLKGYFIWSLMDNFEWAYGYSKRFGITVDYNIQKRILKDSALWLKEFLKS | 438 |

THERMOSTABLE β-GLUCOSIDASE

TECHNICAL FIELD

The present invention relates to a thermostable β-glucosidase, a polynucleotide that encodes the aforementioned thermostable β-glucosidase, an expression vector for expressing the aforementioned thermostable β-glucosidase, a transformant incorporated with the aforementioned expression vector, and a method for producing a cellulose degradation product using the aforementioned thermostable β-glucosidase.

Priority is claimed on Japanese Patent Application No. 2014-184909, filed Sep. 11, 2014, the content of which is incorporated herein by reference.

BACKGROUND ART

Plant biomass or lignocellulose is the most abundant renewable energy source on earth. From the viewpoints of global environmental conservation and fossil fuel depletion, the biorefinery using plant biomass as a biofuel or a raw material of chemical products such as ethanol has attracted attention. The main component in the dry weight of plant biomass is lignocellulose composed of polysaccharides, such as celluloses and hemicelluloses, and lignin. Polysaccharides are hydrolyzed into monosaccharides such as glucose and xylose by glycoside hydrolases, and are then used as a biofuel or a raw material of chemical products.

Lignocellulose having a complex structure is persistent and is difficult to degrade or hydrolyze with a single glycoside hydrolase enzyme. For the complete degradation of lignocellulose, in general, three types of enzymes, i.e., an endoglucanase (cellulase or endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21) are required. In addition, it is considered that an appropriate formulation of multiple enzymes is necessary, including a xylanase (endo-1,4-β-xylanase, EC 3.2.1.8) which is a hemicellulase and other plant cell wall degrading enzymes.

When cellulose is subjected to hydrolysis by cellobiohydrolase, cellobiose which is a disaccharide is mainly produced. β-glucosidase hydrolyzes this cellobiose into glucose, which is a monosaccharide, and is therefore one of the essential enzymes for degrading lignocellulose ultimately to monosaccharides.

In the conventional lignocellulose to ethanol conversion process, high-solid loading up to 30-60% in initial substrate concentration has been attempted for the purpose of higher energy efficiency and less water usage. The enzymatic hydrolysis of lignocellulose by such high-solid loading processes results in the high viscosity of the hydrolyzed biomass solution so that the hydrolysis of lignocellulose hardly proceeds. Therefore, for example, by carrying out the enzymatic hydrolysis process at a high temperature of 80° C. or higher using a thermostable enzyme, in addition to an increase in the hydrolysis reaction rate, since the viscosity of the hydrolyzed biomass solution also reduces, the shortening of the hydrolysis reaction time and the reduction of the amount of enzyme are expected to be achieved. For this reason, for various glycoside hydrolases, development of enzymes that are more excellent in terms of thermostability has been desired.

Many thermostable glycoside hydrolases have been obtained by isolating and identifying the thermophilic microorganisms that live in a high temperature environment, cloning the genes from these cultured and isolated microorganisms and determining the DNA sequence thereof, followed by the expression thereof using *Escherichia coli*, filamentous fungi and the like. For example, a thermostable β-glucosidase (with an optimum temperature of 70° C. and an optimum pH of 3.5 to 4.0) derived from a filamentous fungus *Acremonium cellulolyticus* has been disclosed in Patent Document 1. Three types of thermostable β-glucosidases (with an optimum temperature of 55° C. and an optimum pH of 4.5 to 5.1) derived from *Acremonium cellulolyticus* have been disclosed in Patent Document 2. A thermostable β-glucosidase (with an optimum temperature of 80° C. and an optimum pH of 5 to 6) derived from a *Thermoanaerobactor* species has been disclosed in Patent Document 3. A thermostable β-glucosidase (with an optimum temperature of 80° C. and an optimum pH of 4.6) derived from *Thermoascas auranticus* has been disclosed in Non-Patent Document 1. A thermostable β-glucosidase (with an optimum temperature of 90° C. and an optimum pH of 6 to 7) derived from *Fervidobacterium islandicum* has been disclosed in Non-Patent Document 2.

PRIOR ART DOCUMENTS

Patent Documents

[Patent Document 1] Japanese Patent No. 4801872
[Patent Document 2] Japanese Patent No. 4689807
[Patent Document 3] Japanese Unexamined Patent Application, First Publication No. Hei 10-52274

Non-Patent Documents

[Non-Patent Document 1] Neil et al., Biochemical Journal, 2001, vol. 353, p. 117-127.
[Non-Patent Document 2] Jabbour et al., Applied Microbiology and Biotechnology, 2012, vol. 93, p. 1947-1956.

SUMMARY OF THE INVENTION

Problems to be Solved by the Invention

It is an object of the present invention to provide a novel thermostable β-glucosidase which exhibits hydrolytic activity using p-nitrophenyl-β-D-glucopyranoside (hereinafter, may be abbreviated as PNPG) as a substrate at least under conditions of a temperature of 75° C and a pH of 7, a polynucleotide that encodes the aforementioned thermostable β-glucosidase, an expression vector for expressing the aforementioned thermostable β-glucosidase, a transformant incorporated with the aforementioned expression vector, and a method for producing a cellulose degradation product using the aforementioned thermostable β-glucosidase.

Means for Solving the Problem

In order to solve the above-mentioned problems, the inventors of the present invention have successfully obtained thermostable β-glucosidases having novel amino acid sequences by extracting DNA directly from hot spring high temperature soils and conducting large-scale metagenome sequencing of hardly culturable microbiota. This has led to the completion of the present invention.

That is, as the thermostable β-glucosidase, polynucleotide, expression vector, transformant, method for producing a thermostable β-glucosidase, glycoside hydrolase mixture and method for producing a cellulose degradation product according to the present invention, the following aspects [1] to [10] can be mentioned.

[1] A thermostable β-glucosidase including a β-glucosidase catalytic domain, the β-glucosidase catalytic domain including: (A) a polypeptide including an amino acid sequence represented by SEQ ID NO: 1;
(B) a polypeptide including an amino acid sequence in which at least one amino acid is deleted, substituted, or added in the amino acid sequence represented by SEQ ID NO: 1, and having hydrolytic activity using p-nitrophenyl-β-D-glucopyranoside as a substrate at least under conditions of a temperature of 75° C. and a pH of 7; or
(C) a polypeptide including an amino acid sequence having at least 90% sequence identity with the amino acid sequence represented by SEQ ID NO: 1, and having hydrolytic activity using p-nitrophenyl-β-D-glucopyranoside as a substrate at least under conditions of a temperature of 75° C. and a pH of 7.

[2] The thermostable β-glucosidase according to the aforementioned aspect [1], which also has xylanase activity.

[3] A polynucleotide including a region that encodes a β-glucosidase catalytic domain which includes: (a) a nucleotide sequence that encodes a polypeptide including an amino acid sequence represented by SEQ ID NO: 1;
(b) a nucleotide sequence that encodes a polypeptide including an amino acid sequence in which at least one amino acid is deleted, substituted, or added in the amino acid sequence represented by SEQ ID NO: 1, and having hydrolytic activity using p-nitrophenyl-β-D-glucopyranoside as a substrate at least under conditions of a temperature of 75° C. and a pH of 7;
(c) a nucleotide sequence that encodes a polypeptide including an amino acid sequence having at least 90% sequence identity with the amino acid sequence represented by SEQ ID NO: 1, and having hydrolytic activity using p-nitrophenyl-β-D-glucopyranoside as a substrate at least under conditions of a temperature of 75° C. and a pH of 7;
(d) a nucleotide sequence having at least 80% sequence identity with a nucleotide sequence represented by SEQ ID NO: 2, and encoding a polypeptide having hydrolytic activity using p-nitrophenyl-β-D-glucopyranoside as a substrate at least under conditions of a temperature of 75° C. and a pH of 7; or
(e) a nucleotide sequence of a polynucleotide which hybridizes with a polynucleotide including a nucleotide sequence represented by SEQ ID NO: 2 under a stringent condition, and being a nucleotide sequence that encodes a polypeptide having hydrolytic activity using p-nitrophenyl-β-D-glucopyranoside as a substrate at least under conditions of a temperature of 75° C. and a pH of 7.

[4] The polynucleotide according to the aforementioned aspect [3], wherein the aforementioned polypeptide also has xylanase activity.

[5] An expression vector, which is incorporated with the polynucleotide according to the aforementioned aspect [3] or [4], and which is able to express a polypeptide having β-glucosidase activity in a host cell.

[6] A transformant, which is introduced with the expression vector according to the aforementioned aspect [5].

[7] The transformant according to the aforementioned aspect [6], which is a eukaryotic microbe.

[8] A method for producing a thermostable β-glucosidase, the method including a step of producing a thermostable β-glucosidase in the transformant according to the aforementioned aspect [6] or [7].

[9] A glycoside hydrolase mixture, including the thermostable β-glucosidase according to the aforementioned aspect [1] or [2], a thermostable β-glucosidase encoded by the polynucleotide according to the aforementioned aspect [3] or [4], or a thermostable β-glucosidase produced by the method for producing a thermostable β-glucosidase according to the aforementioned aspect [8], and at least one or more types of other glycoside hydrolases.

[10] A method for producing a lignocellulose degradation product, the method including a step of producing a lignocellulose degradation product containing a cellulose degradation product by bringing a material composed of lignocellulose containing cellulose into contact with the thermostable β-glucosidase according to the aforementioned aspect [1] or [2], a thermostable β-glucosidase encoded by the polynucleotide according to the aforementioned aspect [3] or [4], the transformant according to the aforementioned aspect [6] or [7], a thermostable β-glucosidase produced by the method for producing a thermostable β-glucosidase according to the aforementioned aspect [8], or the glycoside hydrolase mixture according to the aforementioned aspect [9].

Effects of the Invention

The thermostable β-glucosidase according to the present invention has hydrolytic activity using PNPG as a substrate at least under conditions of a temperature of 75° C. and a pH of 7. For this reason, the aforementioned thermostable β-glucosidase is suitable for a hydrolysis process of materials composed of lignocellulose containing cellulose, for example, materials containing a compound having β-glycosidic bonds, under high temperature conditions.

In addition, the polynucleotide, the expression vector incorporated with the aforementioned polynucleotide and the transformant introduced with the aforementioned expression vector according to the present invention are suitably used for the production of the thermostable β-glucosidase according to the present invention.

BRIEF DESCRIPTION OF THE DRAWINGS

FIG. 1 is a pairwise alignment representation of the amino acid sequence (SEQ ID NO: 1) of a β-glucosidase catalytic domain encoded by an open reading frame OJ1G-364 (completely identical with the Oj1G-364-1 gene) and the amino acid sequence of a β-glucosidase (SEQ ID NO: 6) of *Fervidobacterium* sp. YNP.

DESCRIPTION OF THE EMBODIMENT

[Thermostable β-Glucosidase]

Figure 2:
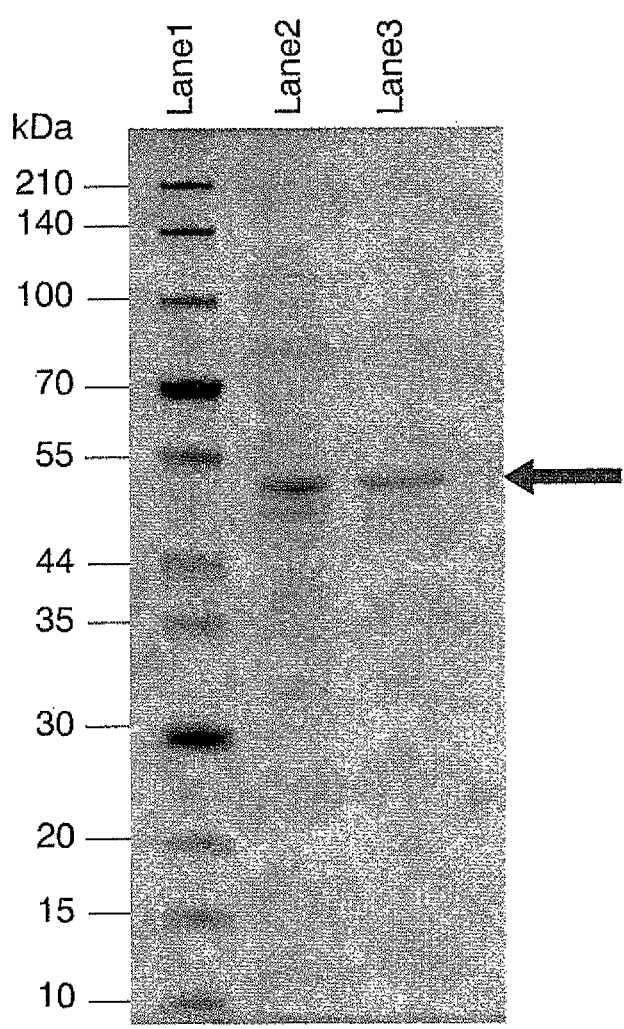
FIG. 2 is a diagram showing the results of SDS-PAGE analysis of the OJ1G-364-1 protein obtained by expressing the OJ1G-364-1 gene in *E. coli* in Example 1.

Many microorganisms including filamentous fungi, bacteria and archaea are difficult to culture, and about 99% of the microorganisms living in the microbial environments such as soil are said to be unknown microbes. In particular, the culturing of microorganisms living in a high temperature environment is extremely difficult, and it is thought that merely 0.1% or less of the microorganisms living in soils have been isolated and cultured with the currently available microbial culturing techniques. This difficulty to culture such microorganisms living in high temperature soils is one factor to hinder the development of thermostable enzymes.

In recent years, because of the development of the next generation giga sequencer enabling large amount sequencing of giga base pairs, it has become possible to conduct the whole genome sequencing of the microbiota contained in soil and the like. Using this analysis technology, the metagenomic analysis method has been proposed in which the genome DNA of a microbial group is prepared from an environmental sample such as soil, the genomes of the group having nonuniform and miscellaneous genomic organizations are directly and comprehensively sequenced, and the sequenced data are assembled by a parallel computer, so as to thereby reconstruct the genomic sequences of the microbiota. This has contributed to the rapid progress in the genome sequencing of hardly culturable microorganisms.

As shown in Example 1 described later, the inventors of the present invention extracted the genomic DNA (metagenomic DNA) of microbial groups from the collected high temperature hot spring soils (for example, hot spring water of 58 to 78° C. that contains soil, mud, microbial mats, biofilms and the like may be mentioned), and conducted shotgun sequencing and annotation of the metagenomic DNA. By so doing, 291 open reading frames (ORFs) encoding amino acid sequences similar to those of the known β-glucosidase enzymes (for example, amino acid sequences in which an expectation value (E-value) is less than $1e^{-20}$) were obtained. Of these ORFs, primers were designed based on the nucleotide sequence information of 111 ORFs in which the presence of β-glucosidase catalytic domain could be verified, and gene candidates were cloned from the metagenomic DNA of the high temperature hot spring soils by the PCR method. The PCR-cloned DNAs were incorporated into *E. coli*, and proteins encoded by the aforementioned nucleotide sequences were expressed. These were subjected to functional screenings by assays on the PNPG degradation activity. In the end, thermostable β-glucosidases having PNPG degradation activity (hereinafter, may be referred to as "OJ1G-364-1") were obtained from these ORFs. The amino acid sequence of OJ1G-364-1 and the nucleotide sequence encoding the amino acid sequence of OJ1G-364-1 are represented by SEQ ID NO: 1 and SEQ ID NO: 2, respectively.

As shown in Example 1 described later, OJ1G-364-1 exhibited high hydrolysis activity for PNPG, and also exhibited degradation activity for p-nitrophenyl-β-D-xylopyranoside (hereinafter, may be abbreviated as PNPX), xylan, and phosphoric acid swollen Avicel (hereinafter, may be abbreviated as PSA), while exhibiting almost no degradation activity for carboxymethyl cellulose (hereinafter, may be abbreviated as CMC). From this substrate specificity, OJ1G-364-1 is suggested to be a β-glucosidase having β-glucosidase activity and also having a certain level of xylanase activity.

It should be noted that in the present invention and the description of this application, the term "β-glucosidase activity" refers to an activity in which by using a compound containing a β-glycosidic bond as a substrate and performing hydrolysis of the substrate, a monosaccharide can be produced.

The "compound containing a β-glycosidic bond" can be exemplified by, for example, a glucan having a β-glycosidic bond, an oligosaccharide having a β-glycosidic bond, and the like. In addition, in the present invention and the description of this application, the term "xylanase activity" refers to an activity to hydrolyze xylan (xylan hydrolysis activity) by using xylan as a substrate.

In addition, in the present invention and the description of this application, the expression "having activity" or "exhibiting activity" refers to an action on at least one substrate and means that a significant difference occurs in the hydrolyzed amount of reducing ends of the substrate or the color reaction as compared to the negative control.

Therefore, the expression "having β-glucosidase activity" refers to an action on at least a compound containing a β-glycosidic bond as a substrate, and means that a significant difference occurs in the hydrolyzed amount of the reducing ends of the substrate or the color reaction as compared to the negative control.

In addition, as another aspect, the expression "having β-glucosidase activity" refers to an action on at least PNPG as a substrate, and means that a significant difference occurs in the hydrolyzed amount of the reducing ends of the substrate or the color reaction as compared to the negative control.

The expression "having xylanase activity" refers to an action on at least xylan as a substrate, and means that a significant difference occurs in the hydrolyzed amount of reducing ends of the substrate or the color reaction as compared to the negative control.

In addition, as yet another aspect, the expression "having β-glucosidase activity" means having 3 U/mg or more hydrolytic activity for at least PNPG under condition of a pH of 7.0 and in a temperature range of 50 to 85° C.

Further, as yet another aspect, the expression "having β-glucosidase activity" means having 20 U/mg or more hydrolytic activity for at least PNPG under condition of a temperature of 50 to 80° C. and in a pH range of 5.0 to 8.0.

In addition, the amino acid sequence of OJ1G-364-1 was searched in publicly known amino acid sequence databases, resulting that the amino acid sequence showing the highest sequence identity was of a β-glucosidase (Genbank Registration ID: AAN60220.1) (SEQ ID NO: 6) of *Fervidobacterium* sp. YNP, with the sequence identity (homology) thereof of 88%. From the substrate specificity and the sequence identity of the amino acid sequence with that of the already known proteins, it is clear that OJ1G-364-1 is a novel β-glucosidase having β-glucosidase activity.

OJ1G-364-1 has hydrolytic activity using PNPG as a substrate (β-glucosidase activity) at least under conditions of a temperature of 80° C. and a pH of 7. Actually, as shown in Example 1 <8> described later, OJ1G-364-1 exhibits β-glucosidase activity within a temperature range from 50 to 85° C. More specifically, the β-glucosidase activity of OJ1G-364-1 tended to be increased as the temperature was increased within a range from 50 to 80° C. and tended to be decreased rapidly when the temperature exceeded 80° C.

Generally, in a protein having some kind of bioactivity, one or two or more amino acids can be deleted, substituted, or added, without deteriorating the bioactivity. In other words, also in OJ1G-364-1, one or two or more amino acids can be deleted, substituted, or added, without causing loss of glycoside hydrolytic activity, including β-glucosidase activity.

That is, the thermostable β-glucosidase according to the present invention is a thermostable β-glucosidase having a β-glucosidase catalytic domain which includes any one of the following (A) to (C):
(A) a polypeptide including an amino acid sequence represented by SEQ ID NO: 1 (that is, OJ1G-364-1);
(B) a polypeptide including an amino acid sequence in which at least one amino acid is deleted, substituted, or added in the amino acid sequence represented by SEQ ID NO: 1, as well as having hydrolytic activity using PNPG as a substrate at least under conditions of a temperature of 75° C. and a pH of 7; or
(C) a polypeptide including an amino acid sequence having at least 90% sequence identity with the amino acid sequence represented by SEQ ID NO: 1, as well as having hydrolytic activity using PNPG as a substrate at least under conditions of a temperature of 75° C. and a pH of 7.

In the present invention and the description of this application, a "polypeptide in which an amino acid is deleted" means that a portion of the amino acids which constitute the polypeptide is missing (that is, removed).

In the present invention and the description of this application, a "polypeptide in which an amino acid is substituted" means that an amino acid which constitutes the polypeptide is replaced with a different amino acid.

In the present invention and the description of this application, a "polypeptide in which an amino acid is added" means that a new amino acid is inserted within the polypeptide.

In the aforementioned polypeptide of (B), the number of amino acids to be deleted, substituted, or added in the amino acid sequence represented by SEQ ID NO: 1 is preferably from 1 to 20, more preferably from 1 to 10, and still more preferably from 1 to 5.

In the aforementioned polypeptide of (C), the sequence identity with the amino acid sequence represented by SEQ ID NO: 1 is not particularly limited as long as it is 90% or greater but less than 100%, although it is preferable to be 95% or greater but less than 100%, and more preferably 98% or greater but less than 100%.

It should be noted that the sequence identity (homology) between a pair of amino acid sequences is obtained such that: two amino acid sequences are juxtaposed while having gaps in some parts accounting for insertion and deletion so that the largest numbers of corresponding amino acids can be matched, and the sequence identity is deemed to be the proportion of the matched amino acids relative to the whole amino acid sequences excluding the gaps, in the resulting alignment. The sequence identity between a pair of amino acid sequences can be obtained by using a variety of homology search software publicly known in the art. The sequence identity value between amino acid sequences in the present invention is obtained by calculation on the basis of an alignment obtained from a publicly known homology search software BLASTP.

The aforementioned polypeptides of (B) and (C) may be those that are artificially designed, or may also be homologues of OJ1G-364-1 and the like, or partial proteins thereof.

The aforementioned polypeptides of (A) to (C) may be respectively synthesized in a chemical manner based on the amino acid sequence, or may also be produced by a protein expression system using the polynucleotide according to the present invention that will be described later. In addition, the aforementioned polypeptides of (B) and (C) can also be respectively synthesized artificially based on a polypeptide including the amino acid sequence represented by SEQ ID NO: 1, by using a genetic recombination technique to introduce amino acid mutation(s).

The aforementioned polypeptides of (A) to (C) has hydrolytic activity (that is, β-glucosidase activity) using PNPG as a substrate at least under conditions of a temperature of 75° C. and a pH of 7. For this reason, a thermostable β-glucosidase can be obtained by having any one of the aforementioned polypeptides of (A) to (C) as the β-glucosidase catalytic domain.

The thermostable β-glucosidase according to the present invention uses PNPG as a substrate. The aforementioned thermostable β-glucosidase may also use another type of β-glucan other than PNPG, an oligosaccharide, or the like as a substrate. Examples of those that can also be used as a substrate by the thermostable β-glucosidase according to the present invention other than PNPG include PNPX; a glucan composed of β-1,3 bonds and β-1,4 bonds such as lichenan; xylan; a crystalline cellulose, such as Avicel, a bacterial crystalline cellulose (bacterial microcrystalline cellulose, BMCC) and a filter paper; PSA; CMC, a glucan composed of β-1,4 bonds; an oligosaccharide composed of β-1,4 bonds such as cellobiose; a glucan composed of β-1,3 bonds and β-1,6 bonds such as laminarin; a glucan composed of β-1,3 bonds; a glucan composed of β-1,6 bonds; and an oligosaccharide composed of β-1,6 bonds such as gentiobiose. As the thermostable β-glucosidase according to the present invention, a thermostable β-glucosidase that also uses, in addition to PNPG, at least one member selected from the group consisting of PNPX, PSA, and xylan as a substrate is preferred.

The thermostable β-glucosidase according to the present invention preferably exhibits hydrolytic activity (β-glucosidase activity) using PNPG as a substrate at least under conditions of a pH of 7 within a temperature range from 60 to 80° C., and more preferably within a temperature range from 50 to 85° C. The optimum temperature of the thermostable β-glucosidase according to the present invention is, at least under a condition of a pH of 7, preferably within the range from 60 to 85° C., more preferably within the range from 70 to 85° C., and still more preferably within the range from 75 to 80° C.

Although the optimum pH of the thermostable β-glucosidase according to the present invention varies depending on the reaction temperature, it is within a pH range from 6.0 to 7.5. As the thermostable β-glucosidase according to the present invention, those exhibiting β-glucosidase activity at least within a pH range of 5.0 to 8.0 are preferred, and those exhibiting β-glucosidase activity within a pH range of 4.0 to 8.0 are more preferred.

The thermostable β-glucosidase according to the present invention may also have, in addition to the aforementioned thermostable β-glucosidase activity, another type of cellulose hydrolysis activity other than the β-glucosidase activity. Such another type of cellulose hydrolysis activity can be exemplified by endoglucanase activity, xylanase activity, xylosidase activity, cellobiohydrolase activity, and the like, and xylanase activity is preferred.

The thermostable β-glucosidase according to the present invention may be an enzyme solely consisting of a β-glucosidase catalytic domain which includes any one of the aforementioned polypeptides of (A) to (C), or may further include other domains. Examples of other domains include a domain present in the known β-glucosidases other than the β-glucosidase catalytic domain. For example, the thermostable β-glucosidase according to the present invention also includes enzymes obtained by substituting a β-glucosidase catalytic domain in a publicly known β-glucosidase with the aforementioned polypeptides of (A) to (C).

If the thermostable β-glucosidase according to the present invention further includes, in addition to the β-glucosidase catalytic domain, a domain other than the β-glucosidase catalytic domain, it is preferable to include a cellulose-binding module. The cellulose-binding module may be either on the upstream (N-end side) or the downstream (C-end side) of the β-glucosidase catalytic domain. In addition, the cellulose-binding module and the β-glucosidase catalytic domain may be directly linked, or linked via a linker domain of an appropriate length. The thermostable β-glucosidase according to the present invention is preferably such that the cellulose-binding module is present on the upstream or the downstream of the β-glucosidase catalytic domain via a linker domain, more preferably such that the cellulose-binding module is present on the upstream of the β-glucosidase catalytic domain via a linker domain.

The cellulose-binding module contained in the thermostable β-glucosidase according to the present invention may suffice if it is a domain having an ability to bind to cellulose, for example, a domain having an ability to bind to PSA or a crystalline Avicel. The amino acid sequence thereof is not particularly limited. As the cellulose-binding module, for example, a cellulose-binding module of an already known protein or appropriately modified product thereof may be used. In addition, if the thermostable β-glucosidase according to the present invention has a β-glucosidase catalytic domain and a cellulose-binding module, it is preferable that these are linked via a linker sequence. The amino acid sequence, the length, and the like, of the linker sequence are not particularly limited.

In addition, the thermostable β-glucosidase according to the present invention may also have a signal peptide enabling to transport it to a specific region to effect localization within a cell, or a signal peptide to effect extracellular secretion, at the N end or the C end. Such a signal peptide can be exemplified by an apoplastic transport signal peptide, an endoplasmic reticulum retention signal peptide, a nuclear transport signal peptide, a secretory signal peptide, or the like. The endoplasmic reticulum retention signal peptide can be exemplified by, for example, a signal peptide including a HDEL amino acid sequence, or the like. In those cases where the thermostable β-glucosidase according to the present invention has a signal peptide at the N end or the C end, the thermostable β-glucosidase expressed in a transformant can be secreted outside the cell, or can be localized in the intracellular endoplasmic reticulum, or the like.

In addition, the thermostable β-glucosidase according to the present invention may also be added with, for example, various types of tags at the N end or the C end of the thermostable β-glucosidase, so as to enable easy and convenient purification in a case of the production using an expression system. Regarding such a tag, for example, it is possible to use a tag for usual use in the expression or purification of a recombinant protein, such as a His tag, a HA (hemagglutinin) tag, a Myc tag, and a Flag tag.

[Polynucleotide that Encodes Thermostable β-Glucosidase]

The polynucleotide according to the present invention encodes the thermostable β-glucosidase according to the present invention. The aforementioned thermostable β-glucosidase can be produced by using the expression system of a host made by introducing an expression vector incorporated with the polynucleotide into the host.

More specifically, the polynucleotide according to the present invention is a polynucleotide having a region that encodes a β-glucosidase catalytic domain which includes any one of the following nucleotide sequences (a) to (e).

(a) A nucleotide sequence that encodes a polypeptide including the amino acid sequence represented by SEQ ID NO: 1;

(b) A nucleotide sequence that encodes a polypeptide including an amino acid sequence in which at least one amino acid is deleted, substituted, or added in the amino acid sequence represented by SEQ ID NO: 1, as well as having hydrolytic activity using PNPG as a substrate at least under conditions of a temperature of 75° C. and a pH of 7;

(c) A nucleotide sequence that encodes a polypeptide including an amino acid sequence having at least 90% sequence identity with the amino acid sequence represented by SEQ ID NO: 1, as well as having hydrolytic activity using PNPG as a substrate at least under conditions of a temperature of 75° C. and a pH of 7;

(d) A nucleotide sequence having at least 80% sequence identity with a nucleotide sequence represented by SEQ ID NO: 2, as well as encoding a polypeptide having hydrolytic activity using PNPG as a substrate at least under conditions of a temperature of 75° C. and a pH of 7; or (e) A nucleotide sequence of a polynucleotide which hybridizes with a polynucleotide including a nucleotide sequence represented by SEQ ID NO: 2 under a stringent condition, as well as being a nucleotide sequence that encodes a polypeptide having hydrolysis activity using PNPG as a substrate as a substrate at least under conditions of a temperature of 75° C. and a pH of 7.

It should be noted that in the present invention and the description of this application, a "polynucleotide in which a nucleotide is deleted" means that a portion of the nucleotides which constitute the polynucleotide is missing (that is, removed).

In the present invention and the description of this application, a "polynucleotide in which a nucleotide is substituted" means that a nucleotide which constitutes the polynucleotide is replaced with a different nucleotide.

In the present invention and the description of this application, a "polynucleotide in which a nucleotide is added" means that a new nucleotide is inserted within the polynucleotide.

In the present invention and the description of this application, the term "under a stringent condition" can be exemplified by the method described in Molecular Cloning—A Laboratory Manual Third Edition (Sambrook et al., Cold Spring Harbor Laboratory Press). The example thereof includes a condition in which hybridization is performed by incubation in a hybridization buffer including 6×SSC (composition of 20×SSC: 3M sodium chloride, 0.3M citric acid solution, and pH 7.0), 5×Denhardt's solution (composition of 100×Denhardt's solution: 2 mass % bovine serum albumin, 2 mass % Ficoll, 2 mass % polyvinylpyrrolidone), 0.5 mass % SDS, 0.1 mg/mL salmon sperm DNA, and 50% formamide, at a temperature of 42 to 70° C. for several hours to overnight. The washing buffer for use in the washing after the incubation is preferably 1×SSC solution containing 0.1 mass % SDS, and more preferably 0.1×SSC solution containing 0.1 mass % SDS.

In the aforementioned nucleotide sequences of (a) to (e), it is preferable to select a degenerate codon having high frequency of usage in the host. For example, the above-mentioned nucleotide sequence of (a) may be either the nucleotide sequence represented by SEQ ID NO: 2, or a nucleotide sequence altered to have a codon having high frequency of usage in the host without changing the amino acid sequence to be encoded by the nucleotide sequence represented by SEQ ID NO: 2. Note that, these codons can be altered by a publicly known gene sequence modification technique or artificial gene synthesis.

The polynucleotide including the nucleotide sequence represented by SEQ ID NO: 2 may be synthesized in a chemical manner based on the nucleotide sequence information, or may be obtained as a full length of a gene that encodes OJ1G-364-1 (may be referred to as "OJ1G-364-1 gene" or "gene clone OJ1G-364-1") or a partial region thereof including the β-glucosidase catalytic domain from the natural world by using a genetic recombination technique. The full length of the OJ1G-364-1 gene or the partial region thereof can be obtained by, for example, collecting a sample containing microorganisms from the natural world, and conducting PCR using the genomic DNA recovered from the sample as a template, with a forward primer and a reverse primer designed on the basis of the nucleotide sequence represented by SEQ ID NO: 2 by a conventional method. The cDNA synthesized by a reverse transcription reaction using mRNA recovered from the sample as a template may also be used as a template. Note that, it is preferable that the sample for recovering the nucleic acid serving as a template is a sample collected from a high temperature environment such as hot spring soil.

In the aforementioned nucleotide sequence of (d), the sequence identity with the nucleotide sequence represented by SEQ ID NO: 2 is not particularly limited as long as it is 80% or greater but less than 100%, although it is preferable to be 85% or greater but less than 100%, more preferably 90% or greater but less than 100%, and still more preferably 95% or greater but less than 100%.

Note that, the sequence identity (homology) between a pair of nucleotide sequences is obtained such that: two nucleotide sequences are juxtaposed while having gaps in some parts accounting for insertion and deletion so that the largest numbers of corresponding nucleotides can be matched, and the sequence identity is deemed to be the proportion of the matched nucleotides relative to the whole nucleotide sequences excluding gaps, in the resulting alignment. The sequence identity between a pair of nucleotide sequences can be obtained by using a variety of homology search software publicly known in the art. The sequence identity value between nucleotide sequences in the present invention is obtained by calculation on the basis of an alignment obtained from a publicly known homology search software BLASTN.

For example, the polynucleotide including the aforementioned nucleotide sequence of (b), (c), or (d) can be respectively synthesized artificially by deleting, substituting, or adding one or two or more nucleotides in a polynucleotide including the nucleotide sequence represented by SEQ ID NO: 2. In addition, the aforementioned nucleotide sequence of (b), (c), or (d) may also be a full length sequence of a homologous gene of the OJ1G-364-1 gene or a partial sequence thereof. The homologous gene of the OJ1G-364-1 gene can be obtained by a genetic recombination technique for use in obtaining a homologous gene of a gene whose nucleotide sequence has been already known.

The polynucleotide according to the present invention may have only the region that encodes the β-glucosidase catalytic domain, or may also have a region that encodes a cellulose-binding module, a linker sequence, various types of signal peptides, various types of tags, or the like, in addition to the aforementioned region.

[Expression Vector]

The expression vector according to the present invention is incorporated with the aforementioned polynucleotide according to the present invention, and is able to express a polypeptide having hydrolytic activity using PNPG as a substrate at least under conditions of a temperature of 75° C. and a pH of 7 in a host cell. That is, it is an expression vector which is incorporated with the aforementioned polynucleotide according to the present invention in a state where the aforementioned thermostable β-glucosidase according to the present invention can be expressed. More specifically, it is necessary for the expression vector to be incorporated with an expression cassette including, from the upstream, DNA having a promoter sequence, the aforementioned polynucleotide according to the present invention, and DNA having a terminator sequence. It should be noted that the incorporation of the polynucleotide into the expression vector can be performed by using a well-known genetic recombination technique. It is also possible to use a commercially available expression vector preparation kit for the incorporation of the polynucleotide into the expression vector.

In the present invention and the description of this application, an "expression vector" is a vector including, from the upstream, DNA having a promoter sequence, DNA having a sequence for incorporating foreign DNA, and DNA having a terminator sequence.

The expression vector may be a vector to be introduced into a prokaryotic cell such as E. coli, or to be introduced into a eukaryotic cell such as a yeast, a filamentous fungus, a cultured insect cell, a cultured mammalian cell, or a plant cell. Regarding such an expression vector, an arbitrary expression vector for usual use can be adopted corresponding to the respective host.

It is preferable that the expression vector according to the present invention is an expression vector incorporated with not only the aforementioned polynucleotide according to the present invention but also a drug resistance gene or the like. This is because it makes it easy to screen host cells transformed by the expression vector and untransformed host cells.

The drug resistance gene can be exemplified by a kanamycin resistance gene, a hygromycin resistance gene, a bialaphos resistance gene, or the like.

[Transformant]

The transformant according to the present invention is introduced with the above-mentioned expression vector according to the present invention. In the aforementioned transformant, the thermostable β-glucosidase according to the present invention can be expressed. The host to introduce the expression vector may be a prokaryotic cell such as E. coli or a eukaryotic cell such as a yeast, a filamentous fungus, a cultured insect cell, a cultured mammalian cell, or a plant cell. That is, the transformant according to the present invention is E. coli, a yeast, a filamentous fungus, a cultured insect cell, a cultured mammalian cell, a plant cell, or the like which is introduced with the expression vector according to the present invention. By culturing a transformant of E. coli, the thermostable β-glucosidase according to the present invention can be produced more easily and conveniently with high yield. On the other hand, because proteins are glycosylated in eukaryotic cells, a thermostable β-glucosidase which is more thermostable can be produced by using a transformant of a eukaryotic cell rather than by using a transformant of a prokaryotic cell.

The method to produce the transformant using the expression vector is not particularly limited, and a method for usual use in the production of transformants can be conducted.

The concerned method can be exemplified by an *Agrobacterium*-mediated method, a particle gun method, an electroporation method, a PEG (polyethylene glycol) method, and the like. Of these, if the host is a plant cell, a particle gun method or an *Agrobacterium*-mediated method is preferred.

If a prokaryotic cell, a yeast, a filamentous fungus, a cultured insect cell, a cultured mammalian cell, or the like is used as a host, the obtained transformant is generally able to be cultured by a usual method in the same manner as that of the untransformed host.

[Method for Producing a Thermostable β-Glucosidase]

The method for producing a thermostable β-glucosidase according to the present invention is a method to produce a thermostable β-glucosidase in the aforementioned transformant according to the present invention. When culturing a transformant produced by using the expression vector incorporated with the aforementioned polynucleotide according to the present invention on the downstream of a promoter which has no ability to regulate the timing of the expression or the like, in the transformant, the thermostable β-glucosidase according to the present invention is expressed constitutively. On the other hand, for the transformant produced by using a so-called expression inducible promoter to induce the expression by means of a specific compound, temperature condition, or the like, the thermostable β-glucosidase is expressed in the concerned transformant by culturing the transformant and conducting an induction treatment suitable for the respective expression-inducing condition.

The thermostable β-glucosidase produced by the transformant may be used in a state of being retained in the transformant, or may be extracted/purified from the transformant.

The method to extract or purify the thermostable β-glucosidase from the transformant is not particularly limited as long as the method does not deteriorate the activity of the thermostable β-glucosidase, and the extraction can be done by a method for usual use in the extraction of a polypeptide from cells or biological tissues. The method can be exemplified by a method in which the transformant is immersed in an appropriate extraction buffer to extract the thermostable β-glucosidase, and thereafter the liquid extract and the solid residue are separated. The extraction buffer preferably contains a solubilizing agent such as a surfactant. If the transformant is a plant, the transformant may be previously shredded or crushed before immersing in an extraction buffer. Moreover, as the method for separating the liquid extract and the solid residue, for example, a publicly known solid-liquid separation treatment such as a filtration method, a compression filtration method, or a centrifugation treatment method may be used, or the transformant immersed in an extraction buffer may be squeezed. The thermostable β-glucosidase in the liquid extract can be purified by using a publicly known purification method such as a salting-out method, an ultrafiltration method, or a chromatography method.

If the thermostable β-glucosidase according to the present invention is expressed while the secretory signal peptide is held in the transformant, a solution containing the thermostable β-glucosidase can be easily and conveniently obtained by culturing the transformant and thereafter recovering a culture liquid supernatant made by removal of the transformant from the obtained culture product. Moreover, if the thermostable β-glucosidase according to the present invention has a tag such as a His tag, the thermostable β-glucosidase in a liquid extract or in a culture supernatant can be easily and conveniently purified by an affinity chromatography method using the tag.

In other words, the method for producing a thermostable β-glucosidase according to the present invention includes the culturing of the transformant according to the present invention to produce a thermostable β-glucosidase within the transformant, and, according to need, the extraction and purification of the thermostable β-glucosidase from the transformant.

[Glycoside Hydrolase Mixture]

The glycoside hydrolase mixture according to the present invention can also be used as a mixture containing the aforementioned thermostable β-glucosidase according to the present invention, or a thermostable β-glucosidase produced by the aforementioned method for producing a thermostable β-glucosidase according to the present invention, and at least one or more types of other glycoside hydrolases. The thermostable β-glucosidase produced by the aforementioned method for producing a thermostable β-glucosidase according to the present invention may be in a state of being included in the transformant, or may be extracted or purified from the transformant. By using the thermostable β-glucosidase according to the present invention as a mixture with other glycoside hydrolases in the reaction to degrade a material composed of lignocellulose containing cellulose, the material composed of lignocellulose containing persistent cellulose can be more efficiently degraded.

The other glycoside hydrolase than the aforementioned thermostable β-glucosidase to be contained in the glycoside hydrolase mixture is not particularly limited as long as it has hydrolysis activity for cellulose or hemicellulose. The other glycoside hydrolase than the aforementioned β-glucosidase to be contained in the glycoside hydrolase mixture can be exemplified by hemicellulases such as xylanase or β-xylosidase, cellobiohydrolase, β-glucosidase, endoglucanase, or the like. In addition to the thermostable β-glucosidase, the glycoside hydrolase mixture according to the present invention is preferably a mixture further containing at least either one of glycoside hydrolases (i.e., a hemicellulase or an endoglucanase), and more preferably a mixture containing both of glycoside hydrolases (i.e., a hemicellulase and an endoglucanase). Among them, a mixture further containing, in addition to the thermostable β-glucosidase, at least one of glycoside hydrolases selected from the group consisting of xylanase, β-xylosidase, cellobiohydrolase, and endoglucanase is preferred; and a mixture containing all of glycoside hydrolases (i.e., xylanase, β-xylosidase, cellobiohydrolase, and endoglucanase) is more preferred.

The other glycoside hydrolase to be contained in the glycoside hydrolase mixture is preferably a thermostable glycoside hydrolase having glycoside hydrolysis activity at least at a temperature of 70° C., and more preferably a thermostable glycoside hydrolase having glycoside hydrolysis activity at a temperature of 70 to 85° C. When all the enzymes contained in the glycoside hydrolase mixture are thermostable (for example, the optimum temperature of the enzyme activity or the thermal denaturation temperature of the enzyme protein is 70° C. or higher), the reaction to degrade the material composed of lignocellulose containing cellulose with the glycoside hydrolase mixture can be efficiently conducted under a high temperature condition. That is, if the glycoside hydrolase mixture contains only thermostable glycoside hydrolases, it becomes possible, by using the glycoside hydrolase mixture for the hydrolysis process of a material composed of lignocellulose containing cellulose, to conduct the hydrolysis reaction of the material composed of lignocellulose containing cellulose under a high temperature environment where the hydrolysis temperature is from 70 to 85° C. (high temperature hydrolysis).

With this high temperature hydrolysis, the amount of enzymes and the time for hydrolysis can be remarkably reduced, and the cost for hydrolysis can be largely cut out.

[Method for Producing a Lignocellulose Degradation Product]

The method for producing a lignocellulose degradation product according to the present invention is a method to degrade a material composed of lignocellulose containing cellulose, for example, a material containing a compound with a β-glycosidic bond, to thereby obtain the degradation product thereof, with the thermostable β-glucosidase according to the present invention. More specifically, a material composed of lignocellulose containing cellulose, for example, a material containing a compound with a β-glycosidic bond is brought into contact with the thermostable β-glucosidase according to the present invention, the transformant according to the present invention, a thermostable β-glucosidase produced by the method for producing a thermostable β-glucosidase according to the present invention, or the glycoside hydrolase mixture according to the present invention. By doing so, a lignocellulose degradation product, for example, a degradation product of cellulose (for example, a degradation product in a state where the β-glycosidic bonds in the aforementioned material have been fully or partially degraded, and such a degradation product can be exemplified by monosaccharide such as glucose and xylose, oligosaccharide consisting of such the monosaccharide and the like) is produced.

The material composed of lignocellulose containing cellulose, for example, the material containing a compound with a β-glycosidic bond, is not particularly limited as long as it contains cellulose, for example, a compound containing a β-glycosidic bond. Such a material can be exemplified by cellulose-based biomass such as a weed and an agricultural waste, used paper, or the like. The above material is preferably subjected to a physical treatment such as crushing or shredding, a chemical treatment with an acid, alkali, or the like, or a treatment such as immersing in an appropriate buffer or a dissolution treatment, or the like, prior to being brought into contact with the thermostable β-glucosidase according to the present invention.

The reaction condition of the hydrolysis reaction of the material composed of lignocellulose containing cellulose, for example, the material containing a compound with a β-glycosidic bond by means of the thermostable β-glucosidase according to the present invention may suffice if the condition allows the thermostable β-glucosidase to exhibit β-glucosidase activity. For example, it is preferable to conduct the reaction at a temperature of 50 to 85° C. and a pH of 5.0 to 8.0, more preferable to conduct the reaction at a temperature of 60 to 85° C. and a pH of 5.0 to 7.0, and still more preferable to conduct the reaction at a temperature of 60 to 80° C. and a pH of 5.0 to 7.0. The reaction time of the hydrolysis reaction is appropriately adjusted in consideration of the type, the method of pretreatment, the amount, or the like, of the material composed of lignocellulose containing cellulose to be supplied to the hydrolysis.

For example, the hydrolysis reaction can be carried out in a reaction time of 10 minutes to 100 hours, and 1 to 100 hours when degrading the cellulose-based biomass.

For the hydrolysis reaction of the aforementioned material composed of lignocellulose containing cellulose, it is also preferable to use at least one or more types of other glycoside hydrolases simultaneously or separately, in addition to the thermostable β-glucosidase according to the present invention. The other glycoside hydrolase may be the same as the glycoside hydrolase that can be contained in the aforementioned glycoside hydrolase mixture, and it is preferable to be a thermostable glycoside hydrolase having glycoside hydrolysis activity at least at a temperature of 70° C., and preferably at least at a temperature of 70 to 85° C.

In addition, one aspect of the method for producing a lignocellulose degradation product is the use of the thermostable β-glucosidase according to the present invention, the transformant according to the present invention, or a thermostable β-glucosidase produced by the method for producing a thermostable β-glucosidase according to the present invention, and another aspect is the use of the aforementioned glycoside hydrolase mixture.

EXAMPLES

Next is a more detailed description of the present invention with reference to Examples. However, the present invention is not to be limited to the following Examples.

[Example 1] Cloning of Novel Thermostable β-Glucosidase from Hot Spring Soil

<1> DNA Extraction from Hot Spring Soil and Whole Genome Sequencing (WGS)

With the purpose of searching for genes of novel thermostable β-glucosidase exhibiting activity at a temperature of 70 to 90° C., soil DNA was collected from neutral to weakly alkaline hot springs and subjected to nucleotide sequencing of the metagenomic DNA of the microbiota constituting the soil.

As the soil sample from neutral to weakly alkaline hot springs, hot spring water containing soil, clay, and biomat was collected from five sampling points having gushing high temperature outdoor hot springs in three areas in Japan (metagenomic DNA samples N2, AR19, AR15, OJ1, and H1). These hot spring soil samples were within a range of temperature from 58 to 78° C. and a pH of 7.2 to 8 at the time of the collection.

DNA was extracted from 10 g of each of the collected hot spring soil samples by using the DNA extraction kit (ISOIL Large for Beads ver. 2, manufactured by NIPPON GENE Co., Ltd.). 5 μg of the extracted DNA was subjected to shotgun sequencing of the metagenomic DNA by using the sequencer GS FLX Titanium 454 manufactured by Roche Diagnostics K.K. The remaining DNA was used for PCR cloning of the β-glucosidase gene.

The metagenomic DNA sequencing was carried out using the hot spring soil sample OJ1. By so doing, a data set of the whole genome sequence (WGS) with an average read length of 390 bp, a total read number of 6,301,450, and a total quantity of sequenced genomes of 2,456,206,434 bp, was obtained.

<2> Assembling and Statistics of Hot Spring Metagenomic Data

The output from the Roche 454 (sff file) was rebasecalled with the PyroBayes (Quinlan et al., Nature Methods, 2008, vol. 5, p. 179-81.), by which sequence files and quality files in FASTA format were obtained. After clipping their ends to improve the quality, the obtained sequence reads were assembled with use of the assembly software, Newbler version 2.5.3 of 454 Life Sciences. The assembling was performed by setting "minimum acceptable overlap match (mi)=0.9", and "option:–large (for large or complex genomes, speeds up assembly, but reduces accuracy.)".

The total of the quality filter processed reads and 100 bp or longer assemble contigs was 1.9 Gbp. This data set was used for the β-glucosidase enzyme gene analysis. Out of the total read number of 6,301,450, 3,908,909 reads were assembled into contigs (188,991 contigs in total). Of these, the longest contig length was 278,185 bp.

<3> Prediction of Open Reading Frames (ORFs) of β-Glucosidase

The sequences of EC numbers of 3.2.1.4 (cellulase), 3.2.1.21 (β-glucosidase), 3.2.1.37 (β-glucosidase), 3.2.1.91 (cellulose 1,4-β-cellobiosidase), and 3.2.1.8 (endo 1,4-β-xylanase) were downloaded from the UniProt database (http://www.uniprot.org/) (the date of access: 2009 Apr. 13), and the proteome local database of these glycoside hydrolase genes was constructed. Using the annotation software Metagene (Noguchi et al., DNA Research, 2008, 15(6)), gene regions (=open reading frames) were predicted from the contig sequences obtained from the above-mentioned process <2>. In order to extract the glycoside hydrolase gene from the predicted ORF, the aforementioned local database using BLASTP (blastall ver. 2.2.18) was referred to. Optional conditions of BLASTP were set such that: "Filter query sequence=false", "Expectation value (E) <1e-20" [hereunder, the default values: Cost to open a gap=−1, Cost to extended gap=−1, X dropoff value for gapped alignment=0, Threshold for extending hits=0, and Word size=default], and the ORF sequences that hit any one of Glyco_hydro_3_C, Exo-1,4-beta glucosidase, Beta-glucosidase, Beta-d-glucosidase, B-glucosidase, Xylosidase, Glycoside hydrolase family 1, Glycoside hydrolase family 3, Glycoside hydrolase family 1, Glycoside hydrolase family 3, Beta-D-glucoside glucohydrolase, and Beta-galactosidase that were entered in the aforementioned local database were collected as candidate sequences of β-glucosidase.

<4> Classification of Genes into Glycoside Hydrolase (GH) Families

The candidate sequences of β-glucosidase that had been collected in the above-mentioned process<3> were subjected to functional classification, with reference to the protein functional region sequence database of pfam HMMs (Pfam version 23.0 and HMMER v 2.3; Finn et al., Nucleic Acids Research Database, 2010, Issue 38, p. D211-222). More specifically, the glycoside hydrolase (GH) families were determined by the homology with the Pfam domain database by using the sequence homology search algorithm HMMER to which the hidden Markov model was applied (Durbin et al., "The theory behind profile HMMs. Biological sequence analysis: probabilistic models of proteins and nucleic acids", 1998, Cambridge University Press.; hmmpfam (Ver. 2.3.2), E-value cutoff <1e-5; Database=Pfam_fs (models that can be used to find fragments of the represented domains in a sequence.)).

The result of the GH family classification of 291 ORFs predicted as candidate sequences of β-glucosidase is shown in Table 1. Those that covered 70% or more of the sequence of GH catalytic domain were counted. The sequences exhibiting a coverage of the GH catalytic domain of less than 70% and the sequences whose homologues could not be found in the Pfam database were classified as unknown GH. As shown in Table 1, 14 β-glucosidase ORFs belonging to the GH1 family were obtained. On the other hand, 71 ORF sequences belonging to the GH3 family, 17 ORFs belonging to the GH31 family, and 9 ORFs belonging to the GH43 family were obtained, respectively. Primers were designed for all of these 111 ORFs including incomplete sequences in which the presence of β-glucosidase catalytic domain sequences could be confirmed, and these genes were cloned from the hot spring soil metagenomic DNA by PCR. In the ORF prediction by the Metagene software, initiation codons (L, V) other than methionine (M) were predicted at times,
and the number of full-length ORFs indicated in Table 1 also include ORFs with these initiation codons. For ORFs in which initiation codons are not methionine, primers were designed so as to add the codon sequence of methionine (ATG) to the 3' end of the sequence.

TABLE 1

| OJ1 metagenome | GH family classification of β-glucosidase genes | | | | | | |
|---|---|---|---|---|---|---|---|
| | GH1 | GH3 | GH31 | GH43 | Other GHs | Unknown GHs | Total |
| Full-length ORFs | 13 | 35 | 11 | 6 | 0 | 49 | 114 |
| Incomplete ORFs | 1 | 36 | 6 | 3 | 0 | 131 | 177 |
| Total number of ORFs | 14 | 71 | 17 | 9 | 0 | 180 | 291 |

<5> Open Reading Frame OJ1G-364

The open reading frame OJ1G-364 encoded a polypeptide (SEQ ID NO: 1) including 438 amino acid residues and was a full-length sequence (SEQ ID NO: 2), such that the polypeptide started from methionine which was an amino acid residue at position 1, and the 3' end of the nucleotide sequence encoding the polypeptide ended with a termination codon. From the sequence homology of motifs, 432 amino acids from phenylalanine (F) at position 7 to serine (S) at the end at position 438 in the polypeptide encoded by the open reading frame OJ1G-364 were predicted to be a catalytic domain of the Glycoside hydrolase family 1.

FIG. 1 shows a pairwise alignment of the amino acid sequence of the β-glucosidase catalytic domain of the open reading frame OJ1G-364 (completely identical with the OJ1G-364-1 gene) and the amino acid sequence of the β-glucosidase (Genbank registration ID: AAN60220.1) of Fervidobacterium sp. YNP. In FIG. 1, the black/white inverted amino acids denote the same amino acid residues (identical) throughout all of these amino acid sequences, and the shaded amino acids denote similar amino acid residues (similar) in these amino acid sequences. 388 amino acid residues out of 439 amino acid residues were identical, such that the β-glucosidase catalytic domain of the open reading frame OJ1G-364 showed 88% sequence identity with the β-glucosidase of Fervidobacterium sp. YNP.

<6> Gene Cloning

PCR was conducted using a hot spring soil DNA that had been amplified by the genomic DNA amplification kit (GenomiPhi V2 DNA Amplification Kit, manufactured by GE Healthcare) as a template, and by using a forward primer composed of the nucleotide sequence represented by SEQ ID NO: 5 (5'-CACCATGATAAAGAGATCCGATTTTC-3': obtained by adding 4 nucleotides (CACC) to the 5'-end side of the nucleotide sequence represented by SEQ ID NO: 3. The nucleotides CACC added on the 5' side is a sequence for insertion into a vector) and a reverse primer composed of the nucleotide sequence represented by SEQ ID NO: 4 (5'-TTACGATATGAGGAAATCTTTCAACC-3'). It should be noted that the nucleotide sequence represented by SEQ ID NO: 3 is a nucleotide sequence which is homologous (identical) with a partial sequence including the nucleotides at position 1 to 22 of the nucleotide sequence represented by SEQ ID NO: 2. Moreover, the nucleotide sequence represented by SEQ ID NO: 4 is a nucleotide sequence which is complementary with a partial sequence including the nucleotides at position 1292 to 1317 of the nucleotide sequence represented by SEQ ID NO: 2. The amplified PCR products were inserted in the pET101/D-TOPO vector of Champion pET Directional TOPO Expression Kits (manufactured by Life Technologies), and transformed into the One Shot TOP10 strain. Positive clones were selected by colony PCR, and then cultured in a LB liquid medium containing 100 mg/L ampicillin at a temperature of 37° C. and 200 rpm for 17 to 20 hours, followed by the preparation of plasmids using the miniprep kit (Wizard plus SV Minipreps DNA Purification System, manufactured by Promega). The prepared plasmids were sequenced by using the 3730 DNA Analyzer (manufactured by Life Technologies Corporation).

Two gene clones OJ1G-364-1 and OJ1G-364-7 were obtained from the open reading frame OJ1G-364 by PCR cloning. The nucleotide sequence of OJ1G-364-1 which was a β-glucosidase candidate gene included 1,317 bp in the same manner as the open reading frame OJ1G-364 (SEQ ID NO: 2), and was encoding exactly the same amino acid sequence as that of OJ1G-364. On the other hand, the β-glucosidase candidate gene OJ1G-364-7 was a single amino acid variant of OJ1G-364, and leucine (L) at position 124 in the amino acid sequence of OJ1G-364 (SEQ ID NO: 2) was serine (S).

The polypeptide (OJ1G-364-1) encoded by the β-glucosidase candidate gene OJ1G-364-1 (hereafter, may be referred to as an "OJ1G-364-1 gene") was composed of 438 amino acids, and no signal peptide was detected. OJ1G-364-1 was a polypeptide in which 433 amino acids (K3-L435) from lysine at position 3 to leucine at position 435 showed a partial amino acid sequence of the β-glucosidase catalytic domain belonging to the GH1 family.

<7> Gene Expression and Purification of β-Glucosidase Enzymatic Protein

After the sequencing, the plasmids having the target gene were introduced in E. coli for protein expression by a heat shock method. The BL21 Star (DE3) strain furnished in the Champion pET Directional TOPO Expression Kits (manufactured by Life Technologies) was used as the competent cell for the transformation. E. coli having the target gene was inoculated in a LB medium containing 100 mg/L ampicillin and cultured to about OD600=0.2 to 0.8, which was then added with IPTG (isopropyl-β-D(-)-thiogalactopyranoside), and additionally cultured for 5 to 20 hours. By so doing, the expression induction of the target protein was carried out. After the culture, E. coli was collected by centrifugation, to which 50 mM Tris-HCl buffer (pH 8.0) of ⅒-fold volume of the culture liquid was added and suspended. Thereafter, 5 minutes disrupting and 5 minutes halting processes were repeated 7 to 8 times by using an ultrasonic disruption apparatus, Astrason 3000 (manufactured by Misonix, Inc.). By so doing, the crude extract of the gene recombinant E. coli containing the target protein was obtained. The crude extract of the gene recombinant E. coli was filtrated through a filter (pore diameter ϕ=0.45 μm, manufactured by Millipore), and the yielded filtrate was used as a gene recombinant E. coli homogenate supernatant.

The gene recombinant E. coli homogenate supernatant was loaded onto an ion-exchange column HiTrap Q HP (manufactured by GE Healthcare) equilibrated with 50 mM Tris-HCl buffer (pH 8.0), by which proteins were fractionated with 0 to 50% concentration gradient with 50 mM Tris-HCl buffer (pH 8.0) containing 1M NaCl using a middle-to-high pressure liquid chromatography system AKTA design (manufactured by GE Healthcare). The fractions exhibiting β-glucosidase activity were all mixed and then subjected to solution exchange into 50 mM Tris-HCl buffer (pH 8.0) containing 750 mM ammonium sulfate using a centrifugal ultrafiltration membrane VIVASPIN 20 (manufactured by Sartorius stedim). The fractions with β-glucosidase activity after the solution exchange were loaded onto a hydrophobic interaction separation column HiTrap Phnenyl HP (manufactured by GE Healthcare) equilibrated with the same solution, by which proteins were fractionated with 0 to 100% concentration gradient with 50 mM Tris-HCl buffer (pH 8.0). The fractions exhibiting β-glucosidase activity were all mixed and then concentrated by using the VIVASPIN 20 until the liquid volume reached to about 8 mL. The concentrated sample was added to a gel filtration column Hiload 26/60 superdex 200 pg (manufactured by GE Healthcare) equilibrated with 50 mM Tris-HCl buffer (pH 8.0) containing 150 mM NaCl, and fractionated by flowing the same buffer of 1 to 1.5 fold volume of the column volume at a flow rate of 2 to 3 mL/min The fractions exhibiting β-glucosidase activity were all mixed and then subjected to solution exchange into 50 mM Tris-HCl buffer (pH 8.0) and concentrated. By so doing, a purified enzyme having the final concentration of about 1 mg/mL was obtained.

The gene recombinant E. coli homogenate supernatant and the purified enzyme were checked by SDS-PAGE (SDS-polyacrylamide gel electrophoresis) analysis. The SDS PAGE of the gene recombinant E. coli homogenate supernatant and the purified enzyme were respectively conducted by using the AnykD Criterion TGX Strain-Free Precast Gel (manufactured by Bio-Rad Laboratories, Inc.). The electrophoresis samples prepared by respectively mixing the supernatant or the purified enzyme diluted to 0.13 mg/mL with Tris-SDS βME treatment solution (manufactured by Cosmo Bio Co., Ltd.) at 1:1 were treated at a temperature of 98° C. for 10 minutes. Then, 2.5 μL of the gene recombinant E. coli homogenate supernatant and 10 μL of the purified enzyme per each sample were respectively electrophoresed. After the electrophoresis, the protein bands were visualized by the imaging system ChemiDoc (manufactured by Bio-Rad Laboratories, Inc.).

FIG. 2 shows the SDS-PAGE analysis result of the gene recombinant E. coli homogenate supernatant prepared from the transformed E. coli introduced with the OJ1G-364-1 gene and the purified enzyme which was purified from the gene recombinant E. coli homogenate supernatant. The lane 1 is a molecular weight marker for proteins, and the lanes 2 and 3 show the electrophoresis patterns of the gene recombinant E. coli homogenate supernatant and the purified enzyme, respectively. As a result, in the gene recombinant E. coli homogenate supernatant (lane 2), a strong band was observed near the molecular weight of 50.6 kDa predicted from the amino acid sequence (SEQ ID NO: 1), and in the purified enzyme (lane 3), a single band corresponding with the above band was observed (indicated by an arrow in the figure).

<8> pH and Temperature Dependencies of β-Glucosidase Activity Using PNPG as Substrate PNPG was used as a substrate in the measurement of the β-glucosidase activity. A solution prepared by dissolving PNPG (manufactured by Sigma-Aldrich Co. LLC.) in water and adjusting to a predetermined final concentration was used as a substrate solution. It should be noted that the PNPG aqueous solution prepared by the above method was used as the PNPG substrate solution used for all the following experiments.

The pH dependency of the PNPG hydrolysis activity of the enzymatic protein (OJ1G-364-1) encoded by the OJ1G-364-1 gene was investigated. In the measurement, a purified enzyme solution prepared by diluting the purified enzyme obtained from the above-mentioned process <7> to 0.005 mg/mL with 50 mM Tris-HCl buffer (pH 8.0) was used.

The measurement of the PNPG hydrolysis activity of the purified enzyme was conducted by allowing a mixture solution composed of 50 μL of a 40 mM PNPG aqueous solution, 50 μL of McIlvaine buffer (at a pH of 3.0, 4.0, 5.0, 6.0, 6.5, 7.0 or 8.0), 80 μL of purified water, and 20 μL of the purified enzyme solution, to react at a temperature of 50° C. or 80° C. for 15 minutes (enzyme final concentration: 0.0005 mg/mL, substrate final concentration: 10 mM). In all the measurements, a mixture solution prepared by adding 50 mM Tris-HCl buffer (pH 8.0) in place of the purified enzyme solution and reacting under the same conditions was used as the control lot. Moreover, the substrate solution and the mixture of the purified enzyme solution and purified water and the buffer were respectively and separately kept at retained reaction temperatures for 5 minutes, and then mixed. This timing was set to the initiation of the reaction. During the reaction, all of the mixed solutions were set to a predetermined temperature by using the Thermomixer (manufactured by Eppendorf AG). After the completion of the reaction, the reaction was stopped by adding the same volume of a 0.2 M $Na_2CO_3$ solution to each mixture solution with stirring, followed by centrifugation. By so doing, the supernatant was obtained. The absorbance at 420 nm was measured by using a spectrophotometer, and the amount of p-nitrophenol in the supernatant was calculated by using a calibration curve prepared with p-nitrophenol. The amount of p-nitrophenol produced by the enzymatic hydrolysis was obtained by the difference from the control lot. The enzymatic activity for producing 1 μmol of p-nitrophenol per minute was defined as 1 U, and the value obtained by dividing it by the amount of protein was defined as the specific activity (U/mg). In addition, each measurement was performed by three independent experiments, from which the mean value and the standard errors were obtained.

Then, the temperature dependency of the PNPG hydrolysis activity of the purified OJ1G-364-1 was investigated.

The measurement of the PNPG hydrolysis activity of the purified enzyme was conducted by performing the enzymatic reaction in the same manner as in the case of examining the pH dependency of the PNPG hydrolysis activity of OJ1G-364-1, except for using a phosphoric acid buffer of a pH of 7.0 in place of the McIlvaine buffer and conducting at a reaction temperature of 50, 60, 70, 75, 80, 85, 90, or 99° C. Then, the absorbance at 420 nm of the supernatant of the mixture solution after the reaction was measured to obtain the amount of p-nitrophenol produced by the hydrolysis.

Figure 3:
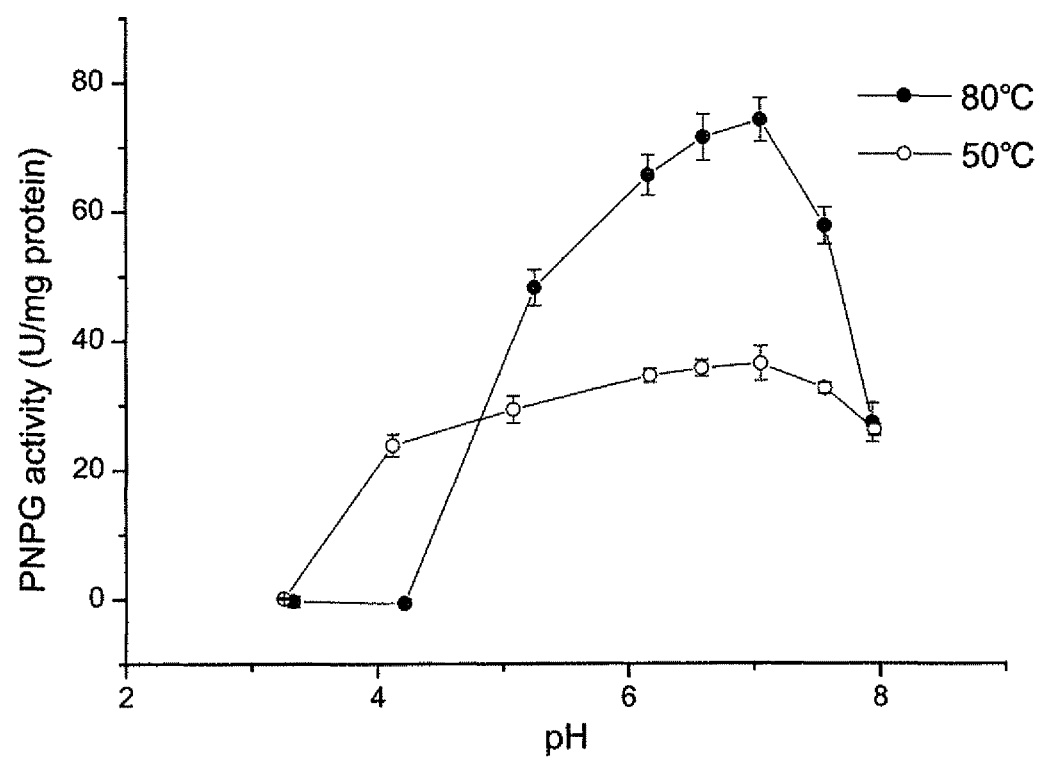
FIG. 3 is a diagram showing the results of the PNPG hydrolysis activity (at 50° C. or 80° C.) of the OJ1G-364-1 protein expressed in *E. coli* measured at respective pH values in Example 1.
Figure 4:
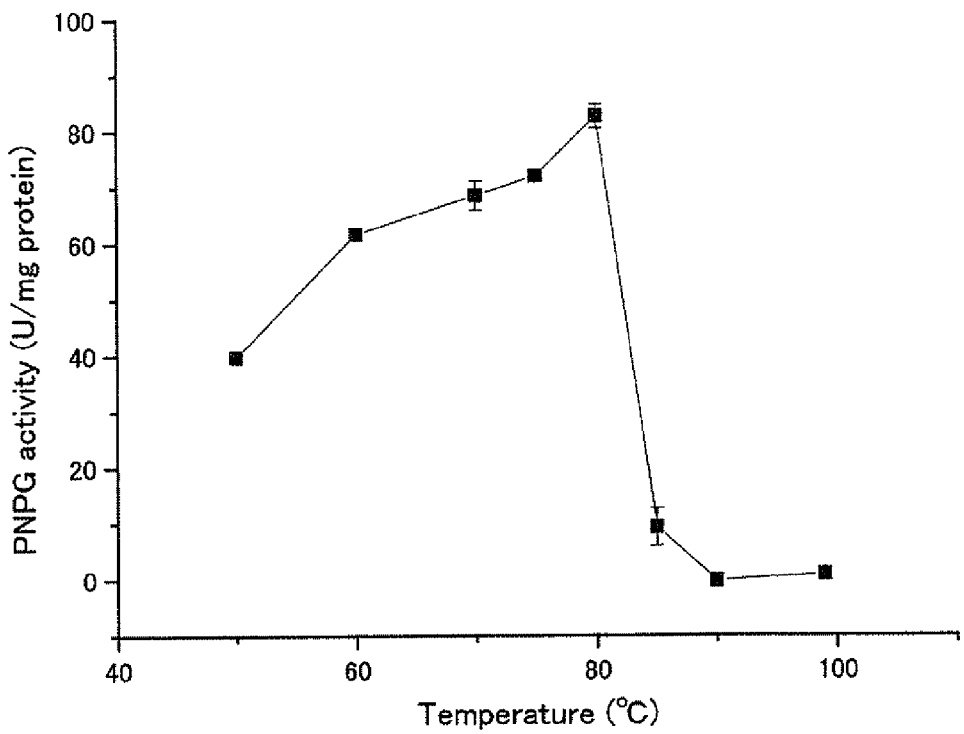
FIG. 4 is a diagram showing the results of the PNPG hydrolysis activity of the OJ1G-364-1 protein expressed in *E. coli* measured at respective temperatures in Example 1.

The measurement results are shown in FIGS. 3 and 4. FIG. 3 is a diagram showing the measurement results of the PNPG hydrolysis activity of the purified enzyme OJ1G-364-1 at a temperature of 50° C. or 80° C. at respective pH values, wherein the horizontal axis represents the pH. FIG. 4 is a diagram showing the measurement results of the PNPG hydrolysis activity (pH 7.0) at respective temperatures, wherein the horizontal axis represents the temperature. The pH was plotted by the actual measurement values of the mixture solution containing the substrate, the buffer, and the enzyme.

The purified enzyme of OJ1G-364-1 exhibited high PNPG hydrolysis activity in a temperature range from 60 to 80° C. (FIG. 4). The optimum temperature ($T_{opt}$) showing the highest activity was 80° C. at a pH of 7.0. When the enzymatic reaction temperature was set to 85° C. or higher, the PNPG hydrolysis activity of the purified enzyme of OJ1G-364-1 was rapidly decreased.

The purified enzyme of OJ1G-364-1 exhibited high PNPG hydrolysis activity within a range of pH 5 to 8 at a reaction temperature from 50 to 80° C. (FIG. 3). The optimum pH varied depending on the reaction temperature, which was a pH of 7.05 (actual measurement value) at a temperature of 50° C., and a pH of 7.1 (actual measurement value) at a temperature of 80° C. A low level of PNPG hydrolysis activity was observed in the purified enzyme of OJ1G-364-1 in ranges of a reaction temperature of 50° C. and a pH of 3.25, and a reaction temperature of 80° C. and a pH of 3.3 to 4.2.

<9> Substrate Specificity of OJ1G-364-1

The hydrolysis activities for various cellulose substrates and hemicellulose substrates were investigated with the enzymatic protein (OJ1G-364-1) encoded by the OJ1G-364-1 gene. In the measurement, a purified enzyme solution prepared by diluting the purified enzyme obtained from the above-mentioned process <7> to 0.005 mg/mL with 50 mM Tris-HCl buffer (pH 8.0) was used. In addition, as substrates, PNPG (manufactured by Sigma-Aldrich Co. LLC.), PNPX (manufactured by Sigma-Aldrich Co. LLC.), CMC (manufactured by Sigma-Aldrich Co. LLC.), PSA, and xylan (derived from beechwood, manufactured by Sigma-Aldrich Co. LLC.) were used.

PSA was prepared by once dissolving an Avicel powder (fine crystalline cellulose powder, manufactured by Merck) with a phosphoric acid solution, then precipitating it by adding sterile purified water, and thereafter washing the same until the pH reached 5 or higher. It should be noted that PSA used for all the following experiments was prepared by the above method.

More specifically, as a reaction solution, a mixture solution composed of 50 μL of phosphoric acid buffer at a pH of 7.0, 20 μL of the purified enzyme solution, the substrate aqueous solution and purified water was used. The concentration and amount of the substrate solution and the amount of purified water to be added to the mixture solution were set in such a manner that 50 μL of a 40 mM substrate aqueous solution and 80 μL of purified water were added when PNPG or PNPX was used as the substrate, 100 μL of a 1% by mass substrate aqueous solution and 30 μL of purified water were added when CMC, PSA or xylan was used as the substrate.

Each mixture solution was incubated at a temperature of 50° C. or 80° C. for 15 minutes to thereby carry out the enzymatic reaction. The substrate solution and the mixture of the purified enzyme solution and purified water and the buffer were respectively and separately kept at retained reaction temperatures for 5 minutes, and then mixed. This timing was set to the initiation of the reaction. In addition, when PSA, and xylan were used as substrates, during the reaction, agitation at 1,400 rpm was applied to the mixture solution using the Thermomixer (manufactured by Eppendorf AG) so as to avoid the precipitation of the substrate.

In the reaction where PNPG or PNPX was used as the substrate, after the completion of the reaction, as in the case of investigating the pH dependency of the PNPG hydrolysis activity of OJ1G-364-1 of the above-mentioned process <8>, the absorbance at 420 nm of the supernatant of the mixture solution after the reaction was measured to obtain the amount of p-nitrophenol produced by the hydrolysis. In the reaction where CMC, PSA, or xylan was used as a substrate, after the completion of the reaction, the same volume of a 3,5-dinitrosalicylic acid reagent (DNS solution) was added. The resulting mixture was treated by heating at a temperature of 100° C. for 5 minutes, cooled down on ice for 5 minutes, and then centrifuged at 17,400 g for 5 minutes at room temperature. By so doing, the supernatant was obtained. The absorbance at 540 nm was measured by using a spectrophotometer, and the amount of reduced sugar in the supernatant was calculated by using a calibration curve prepared with glucose (calibration curve prepared with xylose when xylan was used as a substrate). The amount of reduced sugar produced by the enzymatic hydrolysis was obtained by the difference from the control lot. The enzymatic activity for producing 1 μmol of reduced sugar per minute was defined as 1 U, and the value obtained by dividing it by the amount of protein was defined as the specific activity (U/mg).

Figure 5:
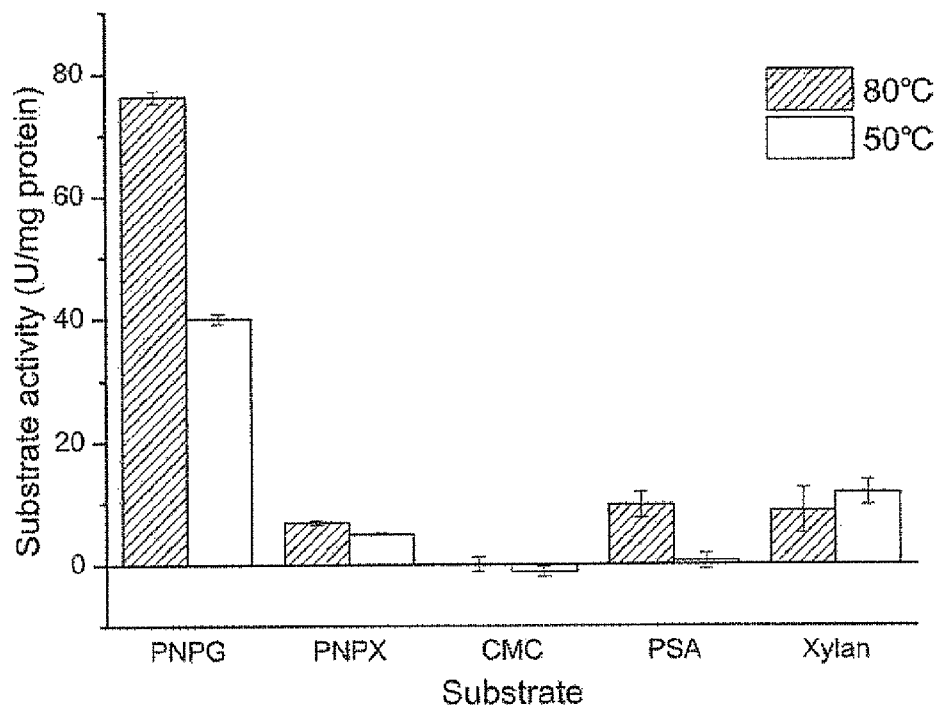
FIG. 5 is a diagram showing the measurement results of the β-glucosidase activity of the OJ1G-364-1 protein expressed in *E. coli* in Example 1 for each substrate.

Each measurement was performed by three independent experiments, from which the mean value and the standard errors were obtained. The measurement results are shown in FIG. 5.

As a result, OJ1G-364-1 exhibited high hydrolysis activity for PNPG, and also exhibited degradation activity for PNPX, xylan, and PSA (only at 80° C.). On the other hand, OJ1G-364-1 exhibited almost no degradation activity for CMC. From these results, it was shown that OJ1G-364-1 was β-glucosidase and also has a certain level of xylanase activity.

<10> Thermal Stability Measurement of β-Glucosidase by Differential Scanning Fluorimetry Differential scanning fluorimetry (DSF) is one of the methods of measuring the thermal denaturation of proteins using a fluorescent dye and a real-time PCR machine, and can be applied to various proteins. The fluorescent dyes used in DSF such as SYPRO Orange emit fluorescence in the nonpolar conditions when binding to the hydrophobic site, while the emission is suppressed in the polar conditions when dissolved in water. Usually, the protein structure is unfolded in the thermal denaturation temperature, and the hydrophobic regions of the protein are exposed to the protein surface. When SYPRO Orange binds to this exposed hydrophobic region, by the excitation light having a wavelength of 470 to 480 nm, strong fluorescence having a peak near a wavelength of 595 nm is emitted. By increasing the temperature of the protein solution at regular intervals in a stepwise manner and measuring the fluorescence intensity, the thermal degradation temperature (=change point of the fluorescence intensity) is calculated.

In the measurement, a purified enzyme solution prepared by adjusting the purified enzyme obtained from the above-mentioned process <7> to 1 mg/mL was used.

More specifically, 2 μL of 100-fold diluted SYPRO Orange (manufactured by Life Technologies), 1 μL of the purified enzyme solution with a concentration of 1 mg/mL, 5 μL of 200 mM phosphoric acid buffer (pH 7.0) and 12 μL of purified water were added into the wells of a 96-well PCR plate (Multiplate 96 Well PCR Plate MLL-9651, manufactured by Bio-Rad Laboratories, Inc.) so that the volume of each well was 20 μL. The PCR plate was sealed with Optical Flat 8-Cap Strips (manufactured by Bio-Rad Laboratories, Inc.), the temperature of the well was increased by 0.2° C. from 30° C. up to 100° C. by a real-time PCR machine (CFX96 Touch Real-Time PCR System, manufactured by Bio-Rad Laboratories, Inc.), and following a lapse of 10 seconds after the target temperature was achieved, the fluorescence intensity of each well was measured simultaneously. SYPRO Orange was excited by a light emitting diode (LED) having a wavelength range of 450 to 490 nm, the SYPRO Orange emitted light was passed through a band pass filter of 560 to 580 nm range, the measurement of the fluorescence intensity was performed with a CCD camera, and changes in the fluorescence intensity were plotted as a function of temperature. The data analysis was carried out using the analysis software CFX Manager (manufactured by Bio-Rad Laboratories, Inc.) supplied with the real-time PCR machine. Each measurement was performed by three independent experiments.

Figure 6:
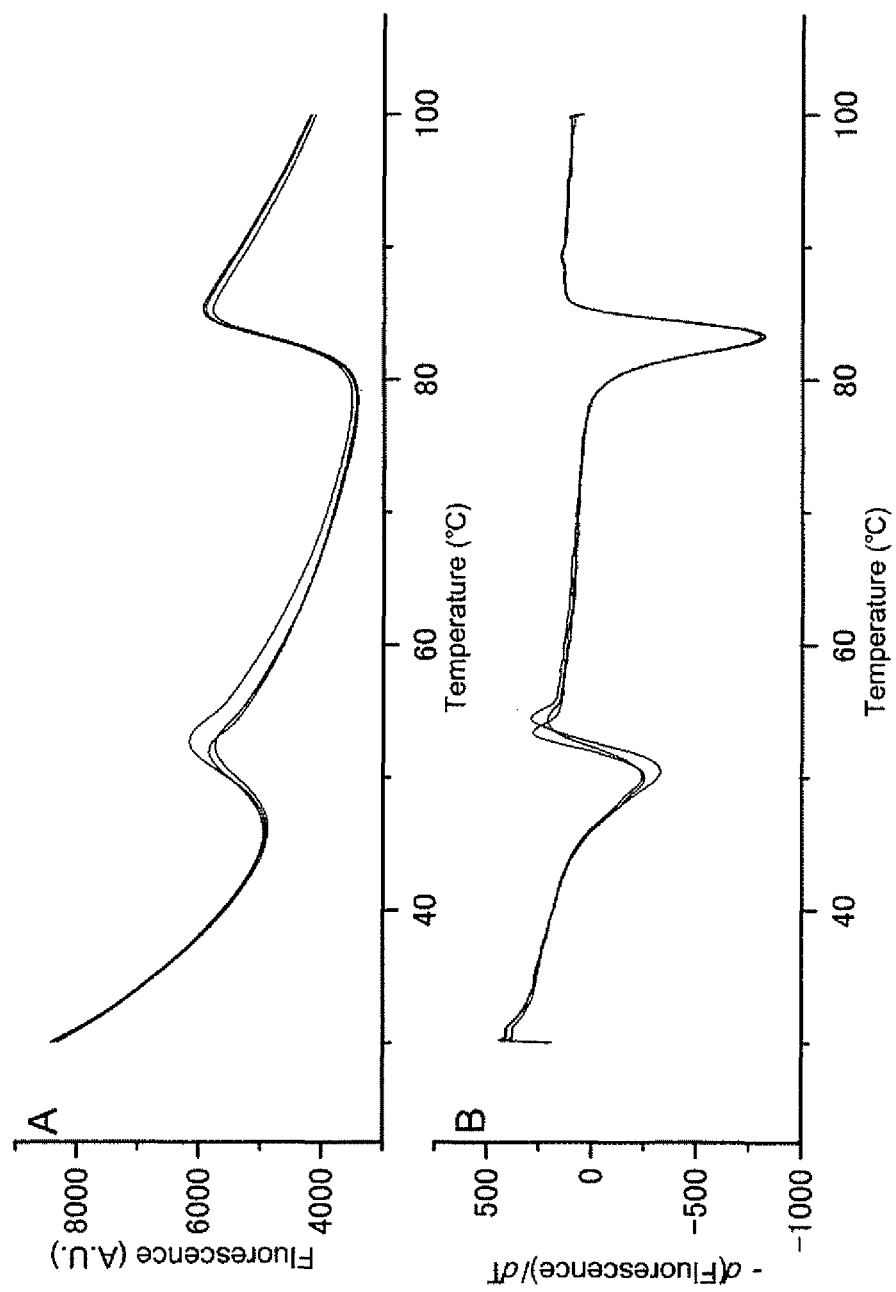
FIG. 6 is a diagram showing a change in the fluorescence intensity of SYPRO Orange caused in association with the thermal denaturation exhibited by the OJ1G-364-1 protein expressed in *E. coli* in Example 1.

FIG. 6 shows changes in the fluorescence intensity of SYPRO Orange caused in association with the thermal denaturation exhibited by the OJ1G-364-1 enzymatic protein which was measured by the DSF method. The upper graph in FIG. 6 shows measured data, and the lower graph in FIG. 6 shows the first derivative "−d(Fluorescence)/dt" of the fluorescence intensity change curve in the upper graph of FIG. 6. The thermal denaturation temperature (melting temperature; Tm value) was defined as the local minimum value of the first derivative ("−d(Fluorescence)/dt" shown on the Y axis of the lower graph in FIG. 6) of the fluorescence intensity curve that is a function of temperature.

In the first derivative of the fluorescence intensity curve of OJ1G-364-1, the local minimum points were observed at two locations near 50° C. and 83° C. Since the OJ1G-364-1 enzymatic protein also exhibited the enzymatic activity in the range of 60° C. to 80° C., it was thought that the local minimum point near 50° C. suggested some sort of structural change in the protein molecule but did not indicate the thermal denaturation, and the actual thermal denaturation temperature was indicated by the local minimum point of around 83° C. The average Tm value of the OJ1G-364-1 enzyme protein was 83.2° C., which was close to the optimum temperature $T_{opt}$=80° C. of the enzyme determined from the β-glucosidase activity.

---

What is claimed is:

1. An isolated recombinant thermostable β-glucosidase comprising:
   a polypeptide consisting of the amino acid sequence of SEQ ID NO: 1 and
   at least one region selected from the group consisting of a cellulose-binding module, linker domain, a signal peptide and a tag.

2. The thermostable β-glucosidase according to claim 1, which also has xylanase activity.

3. A glycoside hydrolase mixture, comprising the thermostable β-glucosidase according to claim 1 and at least one or more types of other glycoside hydrolases.

4. A method for producing a lignocellulose degradation product, the method comprising producing a lignocellulose degradation product containing a cellulose degradation product by bringing a material composed of lignocellulose containing cellulose into contact with the termostable β-glucosidase according to claim 1.

5. A method for producing a lignocellulose degradation product, the method comprising producing a lignocellulose degradation product containing a cellulose degradation product by bringing a material composed of lignocellulose containing cellulose into contact with the glycoside hydrolase mixture according to claim 3.

* * * * *

SEQUENCE LISTING

```
<160> NUMBER OF SEQ ID NOS: 6

<210> SEQ ID NO 1
<211> LENGTH: 438
<212> TYPE: PRT
<213> ORGANISM: Unknown
<220> FEATURE:
<223> OTHER INFORMATION: Amino acid sequence of open reading frame
      OJ1G-364-1

<400> SEQUENCE: 1

Met Ile Lys Arg Ser Asp Phe Pro Lys Asn Phe Val Phe Gly Thr Ala
1               5                   10                  15

Thr Ala Ala Tyr Gln Ile Glu Gly Ala Ala Asn Glu Asp Gly Lys Gly
            20                  25                  30
```

Pro Ser Ile Trp Asp Ile Phe Ser His Thr Pro Gly Lys Ile Met Thr
        35                  40                  45
Gly Glu Asn Gly Asp Val Ala Cys Asp His Tyr His Arg Phe Lys Glu
    50                  55                  60
Asp Val Gln Leu Met Lys Glu Ile Gly Leu Asp Ala Tyr Arg Phe Ser
65                  70                  75                  80
Ile Ser Trp Pro Arg Val Met Pro Asp Gly Lys Asn Ile Asn Gln Lys
                85                  90                  95
Gly Val Asp Phe Tyr Asn Arg Leu Val Asp Glu Leu Leu Glu His Asp
            100                 105                 110
Ile Thr Pro Phe Ile Thr Leu Tyr His Trp Asp Leu Pro Tyr Ala Leu
            115                 120                 125
Tyr Glu Lys Gly Gly Trp Leu Asn Ser Asp Ile Ala Met Tyr Phe Arg
    130                 135                 140
Ala Tyr Ala Thr Phe Met Phe Asn Glu Leu Gly Asp Arg Val Lys His
145                 150                 155                 160
Trp Ile Thr Leu Asn Glu Pro Trp Cys Ser Ser Phe Leu Gly Tyr Phe
                165                 170                 175
Thr Gly Glu His Ala Pro Gly His Lys Asn Leu Gln Glu Ala Ile Val
            180                 185                 190
Ala Ala His Asn Leu Leu Arg Ser His Gly His Ala Val Gln Ser Phe
            195                 200                 205
Arg Glu Glu Val Lys Asp Gly Thr Ile Gly Leu Thr Asn Val Val Met
    210                 215                 220
Lys Val Glu Pro Gly Asp Ser Arg Pro Glu Ser Phe Leu Ala Ala Ser
225                 230                 235                 240
Leu Val Asp Lys Phe Val Asn Ala Trp Phe His Asp Pro Val Val Phe
                245                 250                 255
Gly Lys Tyr Pro Glu Glu Ala Val Lys Val Tyr Gln Glu Arg Gly Leu
            260                 265                 270
Gln Val Met Glu Asn Asp Met Asp Ile Ile Ser Thr Pro Ile Asp Phe
            275                 280                 285
Phe Gly Val Asn Tyr Tyr Thr Arg Thr Leu Val Val Phe Asp Thr Thr
    290                 295                 300
Asn Pro Leu Gly Phe Ser Tyr Val Gln Gly Asp Leu Pro Lys Thr Glu
305                 310                 315                 320
Met Gly Trp Glu Ile Tyr Pro Gln Gly Leu Phe Asp Met Leu Val Thr
                325                 330                 335
Leu Lys Glu Arg Tyr Arg Leu Pro Leu Tyr Ile Thr Glu Asn Gly Met
            340                 345                 350
Ala Gly Pro Asp Lys Ile Glu Asn Gly Lys Val Lys Asp Thr Tyr Arg
            355                 360                 365
Ile Glu Tyr Leu Glu Lys His Phe Lys Ala Leu Glu Ala Ile Asn
    370                 375                 380
Ala Gly Val Asn Leu Lys Gly Tyr Phe Ile Trp Ser Leu Met Asp Asn
385                 390                 395                 400
Phe Glu Trp Ala Tyr Gly Tyr Ser Lys Arg Phe Gly Ile Ile Tyr Val
                405                 410                 415
Asp Tyr Asn Thr Gln Lys Arg Ile Leu Lys Asp Ser Ala Tyr Trp Leu
            420                 425                 430
Lys Asp Phe Leu Ile Ser
            435

<210> SEQ ID NO 2
<211> LENGTH: 1317
<212> TYPE: DNA
<213> ORGANISM: Unknown
<220> FEATURE:
<223> OTHER INFORMATION: Open reading frame OJ1G-364; nucleotide sequence encoding the amino acid sequence of OJ1G-364-1

<400> SEQUENCE: 2

```
atgataaaga gatccgattt tccgaaaaat tttgttttg gaaccgcaac ggctgcttat      60
cagatagagg gggcagcaaa cgaggatgga aaaggtcctt cgatttggga tattttttcg    120
catacccgg gcaagatcat gactggtgaa acggggatg ttgcctgcga tcactatcat      180
cgttttaaag aagatgtcca gttaatgaaa gagataggtt tagacgcgta caggttttca    240
atctcgtggc cccgagtcat gcccgacggg aaaaacatca accaaaaagg tgtggatttt    300
tacaacaggt tagtcgacga gttgcttgaa catgacataa ccccgttcat aacactgtac    360
cactgggatt tgccatacgc actgtacgaa aaaggcggat ggctaaattc agacatcgca    420
atgtacttcc gcgcctacgc gactttcatg ttcaacgaac tcggagatag agttaaacac    480
tggataactc tcaacgagcc atggtgctct tcgttccttg atatttcac cggcgaacac    540
gctcccgggc ataaaaatct tcaagaagcg attgtagcag ctcacaattt attgagatca    600
cacggtcacg ctgtccaatc tttcagaaga gaggtaaaag atggaactat cggacttact    660
aacgtcgtta tgaaagtaga acccggcgat tcaaggccag agagtttcct cgcagcttcg    720
ctagtcgaca gtttgtaaa cgcttggttc catgaccctg ttgtctttgg aaagtatccc    780
gaagaagccg tcaaggttta tcaggaacga gggcttcagg taatggaaaa cgacatggac    840
attatatcta ctcctattga tttcttcggt gtaaattact acacgagaac gcttgtcgta    900
tttgatacaa ctaatccgtt gggattttcg tacgtccaag gcgacttgcc gaagaccgag    960
atgggctggg agatttatcc gcaaggctta tttgatatgc ttgtcacact gaaagaaaga   1020
tacagattac ctcttttatat aacagaaaac ggaatggctg accagataa gatagaaaat   1080
ggaaaggtaa aagataccta cagaattgaa tatttagaaa acatttttga aaggcattg    1140
gaagcgataa acgcaggagt gaatttgaaa ggttatttca tctggtcttt gatggataac   1200
ttcgaatggg cttatgggta ttcgaaacgc ttcggaataa tatacgtcga ttacaacacg   1260
cagaaacgta ttttgaaaga ctctgcgtac tggttgaaag atttcctcat atcgtaa      1317
```

<210> SEQ ID NO 3
<211> LENGTH: 22
<212> TYPE: DNA
<213> ORGANISM: Artificial Sequence
<220> FEATURE:
<223> OTHER INFORMATION: Primer; nucleotide sequence which is homologous (identical) with a partial sequence including the nucleotides at position 1 to 22 of the nucleotide sequence represented by SEQ ID NO: 2

<400> SEQUENCE: 3

```
atgataaaga gatccgattt tc                                              22
```

<210> SEQ ID NO 4
<211> LENGTH: 26
<212> TYPE: DNA
<213> ORGANISM: Artificial Sequence
<220> FEATURE:
<223> OTHER INFORMATION: Reverse primer; a nucleotide sequence which is complementary with a partial sequence including the nucleotides at position 1292 to 1317 of the nucleotide sequence represented by -continued

SEQ ID NO: 2

<400> SEQUENCE: 4
ttacgatatg aggaaatctt tcaacc                                           26

<210> SEQ ID NO 5
<211> LENGTH: 26
<212> TYPE: DNA
<213> ORGANISM: Artificial Sequence
<220> FEATURE:
<223> OTHER INFORMATION: Forward primer composed of nucleotide sequence

<400> SEQUENCE: 5
caccatgata aagagatccg attttc                                           26

<210> SEQ ID NO 6
<211> LENGTH: 438
<212> TYPE: PRT
<213> ORGANISM: Unknown
<220> FEATURE:
<223> OTHER INFORMATION: Amino acid sequence; beta-glucosidase of
      Fervidobacterium sp. YNP

<400> SEQUENCE: 6

Met Ile Arg Arg Ser Asp Phe Pro Lys Asp Phe Ile Phe Gly Thr Ala
1               5                   10                  15

Thr Ala Ala Tyr Gln Ile Glu Gly Ala Ala Asn Glu Asp Gly Arg Gly
            20                  25                  30

Pro Ser Ile Trp Asp Val Phe Ser His Thr Pro Gly Lys Thr Leu Asn
        35                  40                  45

Gly Asp Thr Gly Asp Val Ala Cys Asp His Tyr His Arg Tyr Lys Glu
    50                  55                  60

Asp Ile Gln Leu Met Lys Glu Ile Gly Leu Asp Ala Tyr Arg Phe Ser
65                  70                  75                  80

Ile Ser Trp Pro Arg Ile Met Pro Asp Gly Lys Asn Ile Asn Gln Lys
                85                  90                  95

Gly Val Asp Phe Tyr Asn Arg Leu Val Asp Glu Leu Leu Lys Asn Asp
            100                 105                 110

Ile Ile Pro Phe Val Thr Leu Tyr His Trp Asp Leu Pro Tyr Ala Leu
        115                 120                 125

Tyr Glu Lys Gly Gly Trp Leu Asn Pro Asp Ile Ala Leu Tyr Phe Arg
    130                 135                 140

Ala Tyr Ala Thr Phe Met Phe Asn Glu Leu Gly Asp Arg Val Lys His
145                 150                 155                 160

Trp Ile Thr Leu Asn Glu Pro Trp Cys Ser Ser Phe Leu Gly Tyr Tyr
                165                 170                 175

Thr Gly Glu His Ala Pro Gly His Gln Asn Leu Gln Glu Ala Ile Ile
            180                 185                 190

Ala Ala His Asn Leu Leu Arg Ala His Gly His Ala Val Gln Ala Phe
        195                 200                 205

Arg Glu Glu Val Lys Asp Gly Lys Val Gly Leu Thr Asn Val Val Met
    210                 215                 220

Lys Ile Glu Pro Gly Asp Ala Lys Pro Glu Ser Phe Leu Val Ala Ser
225                 230                 235                 240

Leu Val Asp Lys Phe Val Asn Ala Trp Phe His Asp Pro Val Val Phe
                245                 250                 255

Gly Lys Tyr Pro Glu Glu Ala Val Ala Leu Tyr Thr Glu Lys Gly Leu
            260                 265                 270

```
Gln Val Pro Asp Ser Asp Met Asn Ile Ile Ser Thr Pro Ile Asp Phe
    275                 280                 285

Phe Gly Val Asn Tyr Tyr Thr Arg Thr Leu Val Val Phe Asp Met Asn
    290                 295                 300

Asn Pro Leu Gly Phe Ser Tyr Val Gln Gly Asp Leu Pro Lys Thr Glu
305                 310                 315                 320

Met Gly Trp Glu Ile Tyr Pro Gln Gly Leu Phe Asp Met Leu Val Tyr
                325                 330                 335

Leu Lys Glu Arg Tyr Lys Leu Pro Leu Tyr Ile Thr Glu Asn Gly Met
                340                 345                 350

Ala Gly Pro Asp Lys Leu Glu Asn Gly Arg Val His Asp Asn Tyr Arg
                355                 360                 365

Ile Glu Tyr Leu Glu Lys His Phe Glu Lys Ala Leu Glu Ala Ile Asn
    370                 375                 380

Ala Gly Val Asp Leu Lys Gly Tyr Phe Ile Trp Ser Leu Met Asp Asn
385                 390                 395                 400

Phe Glu Trp Ala Tyr Gly Tyr Ser Lys Arg Phe Gly Ile Ile Tyr Val
                405                 410                 415

Asp Tyr Asn Thr Gln Lys Arg Ile Leu Lys Asp Ser Ala Leu Trp Leu
                420                 425                 430

Lys Glu Phe Leu Lys Ser
                435
```